(12) United States Patent
Whitman

(10) Patent No.: US 9,662,514 B2
(45) Date of Patent: *May 30, 2017

(54) BIPOLAR OR ULTRASONIC SURGICAL DEVICE

(71) Applicant: COVIDIEN LP, Mansfield, MA (US)

(72) Inventor: Michael P. Whitman, New Hope, PA (US)

(73) Assignee: Covidien LP, Mansfield, MA (US)

( * ) Notice: Subject to any disclaimer, the term of this patent is extended or adjusted under 35 U.S.C. 154(b) by 323 days.

This patent is subject to a terminal disclaimer.

(21) Appl. No.: 14/493,638

(22) Filed: Sep. 23, 2014

(65) Prior Publication Data
US 2015/0011988 A1 Jan. 8, 2015

Related U.S. Application Data

(60) Continuation of application No. 13/967,441, filed on Aug. 15, 2013, now Pat. No. 8,845,665, which is a
(Continued)

(51) Int. Cl.
*A61N 7/02* (2006.01)
*A61B 17/32* (2006.01)
(Continued)

(52) U.S. Cl.
CPC .................. *A61N 7/02* (2013.01); *A61B 5/01* (2013.01); *A61B 5/4836* (2013.01);
(Continued)

(58) Field of Classification Search
CPC .......... A61B 17/320068; A61B 17/068; A61B 17/320092; A61B 17/285;
(Continued)

(56) References Cited

U.S. PATENT DOCUMENTS

| 659,409 A | 10/1900 | Mosher |
| 1,586,645 A | 6/1926 | Bierman |

(Continued)

FOREIGN PATENT DOCUMENTS

| DE | 4040537 A1 | 8/1991 |
| EP | 0408160 A1 | 1/1991 |

(Continued)

OTHER PUBLICATIONS

"The Cavitron Bipolar Coagulator", Cavitron Surgical Systems, 1979.

(Continued)

*Primary Examiner* — Michael Peffley

(57) ABSTRACT

An electro-mechanical surgical device, system and/or method may include a housing, at least two opposing jaw, and at least one electrical contact associated with at least one of the jaws. The electrical contact may include at least one of a bipolar electrical contact and an ultrasonic electrical contact. The electrical contact may be a row of electrodes located on one or all of the jaws. A sensor may also be associated with any tissue located between the jaws to sense and report the temperature of that tissue. A pierceable ampulla containing fluid may also be placed on at least one of the jaws so that the fluid is releasable when the jaws are in closed position and the electrode(s) pass through the tissue into the pierceable ampulla.

12 Claims, 22 Drawing Sheets

Related U.S. Application Data continuation of application No. 13/611,273, filed on Sep. 12, 2012, now Pat. No. 8,523,890, which is a division of application No. 10/128,768, filed on Apr. 22, 2002, now Pat. No. 8,292,888.

(60) Provisional application No. 60/285,113, filed on Apr. 20, 2001, provisional application No. 60/289,370, filed on May 8, 2001.

(51) Int. Cl.
| | | |
|---|---|---|
| *A61B 18/14* | (2006.01) | |
| *A61B 5/01* | (2006.01) | |
| *A61B 5/00* | (2006.01) | |
| *A61B 17/068* | (2006.01) | |
| *A61B 90/98* | (2016.01) | |
| A61B 17/072 | (2006.01) | |
| A61B 17/285 | (2006.01) | |

(52) U.S. Cl.
CPC .... *A61B 17/068* (2013.01); *A61B 17/320068* (2013.01); *A61B 17/320092* (2013.01); *A61B 18/1442* (2013.01); *A61B 90/98* (2016.02); A61B 17/07207 (2013.01); A61B 17/285 (2013.01); A61B 18/1477 (2013.01); A61B 2018/145 (2013.01); A61B 2018/1425 (2013.01)

(58) Field of Classification Search
CPC ...... A61B 17/07207; A61B 2018/1425; A61B 2018/145; A61B 18/1445; A61B 18/1442; A61N 7/02
See application file for complete search history.

(56) References Cited

U.S. PATENT DOCUMENTS

| | | |
|---|---|---|
| 1,798,902 A | 3/1931 | Raney |
| 1,881,250 A | 10/1932 | Tomlinson |
| 2,031,682 A | 2/1936 | Wappler et al. |
| 2,433,067 A | 12/1947 | Russell |
| 2,448,741 A | 9/1948 | Scott et al. |
| 2,926,232 A | 2/1960 | Gard |
| 3,042,101 A | 6/1962 | Spunt |
| 3,460,539 A | 8/1969 | Anhalt, Sr. |
| 3,651,811 A | 3/1972 | Hildebrandt et al. |
| 3,685,518 A | 8/1972 | Beuerle et al. |
| 3,730,188 A | 5/1973 | Ellman |
| 3,768,482 A | 10/1973 | Shaw |
| 3,826,263 A | 7/1974 | Cage et al. |
| 3,858,586 A | 1/1975 | Lessen |
| 3,920,021 A | 11/1975 | Hiltebrandt |
| 3,934,115 A | 1/1976 | Peterson |
| 3,952,748 A | 4/1976 | Kaliher et al. |
| 3,970,088 A | 7/1976 | Morrison |
| 3,987,795 A | 10/1976 | Morrison |
| RE29,088 E | 12/1976 | Shaw |
| 4,003,380 A | 1/1977 | Wien |
| 4,016,881 A | 4/1977 | Rioux et al. |
| 4,016,886 A | 4/1977 | Doss et al. |
| 4,033,351 A | 7/1977 | Hetzel |
| 4,041,952 A | 8/1977 | Morrison, Jr. et al. |
| 4,043,342 A | 8/1977 | Morrison, Jr. |
| 4,085,756 A | 4/1978 | Weaver |
| 4,092,986 A | 6/1978 | Schneiderman |
| 4,128,099 A | 12/1978 | Bauer |
| 4,161,950 A | 7/1979 | Doss et al. |
| 4,207,896 A | 6/1980 | Shaw |
| 4,220,154 A | 9/1980 | Semm |
| 4,228,800 A | 10/1980 | Degler, Jr. et al. |
| 4,232,676 A | 11/1980 | Herczog |
| 4,248,231 A | 2/1981 | Herczog et al. |
| 4,334,539 A | 6/1982 | Childs et al. |
| 4,353,371 A | 10/1982 | Cosman |
| 4,370,980 A | 2/1983 | Lottick |
| 4,402,311 A | 9/1983 | Hattori |
| 4,483,338 A | 11/1984 | Bloom et al. |
| 4,492,231 A | 1/1985 | Auth |
| 4,494,549 A | 1/1985 | Namba et al. |
| 4,566,456 A | 1/1986 | Koning et al. |
| 4,590,934 A | 5/1986 | Malis et al. |
| 4,593,679 A | 6/1986 | Collins |
| 4,655,216 A | 4/1987 | Tischer |
| 4,657,017 A | 4/1987 | Sorochenko |
| 4,671,274 A | 6/1987 | Sorochenko |
| 4,672,961 A | 6/1987 | Davies |
| 4,674,498 A | 6/1987 | Stasz |
| 4,674,499 A | 6/1987 | Pao |
| 4,674,515 A | 6/1987 | Andou et al. |
| 4,682,596 A | 7/1987 | Bales et al. |
| 4,732,156 A | 3/1988 | Nakamura |
| 4,785,807 A | 11/1988 | Blanch |
| 4,819,633 A | 4/1989 | Bauer et al. |
| 4,848,337 A | 7/1989 | Shaw et al. |
| 4,850,353 A | 7/1989 | Stasz et al. |
| 4,928,699 A | 5/1990 | Sasai |
| 4,931,047 A | 6/1990 | Broadwin et al. |
| 4,955,882 A | 9/1990 | Hakky |
| 4,969,885 A | 11/1990 | Farin |
| 4,985,030 A | 1/1991 | Melzer et al. |
| 4,994,060 A | 2/1991 | Rink et al. |
| 5,007,908 A | 4/1991 | Rydell |
| 5,009,656 A | 4/1991 | Reimels |
| 5,015,227 A | 5/1991 | Broadwin et al. |
| 5,035,696 A | 7/1991 | Rydell |
| 5,047,026 A | 9/1991 | Rydell |
| 5,080,660 A | 1/1992 | Buelna |
| 5,084,045 A | 1/1992 | Helenowski |
| 5,098,431 A | 3/1992 | Rydell |
| 5,108,391 A | 4/1992 | Flachenecker et al. |
| 5,147,356 A | 9/1992 | Bhatta |
| 5,147,357 A | 9/1992 | Rose et al. |
| 5,147,380 A | 9/1992 | Hernandez et al. |
| 5,151,085 A | 9/1992 | Sakurai et al. |
| 5,151,102 A | 9/1992 | Kamiyama et al. |
| 5,171,251 A | 12/1992 | Bregen et al. |
| 5,173,133 A | 12/1992 | Morin et al. |
| 5,207,691 A | 5/1993 | Nardella |
| 5,217,460 A | 6/1993 | Knoepfler |
| 5,221,279 A | 6/1993 | Cook et al. |
| 5,221,281 A | 6/1993 | Klicek |
| 5,250,047 A | 10/1993 | Rydell |
| 5,251,613 A | 10/1993 | Adair |
| 5,254,117 A | 10/1993 | Rigby et al. |
| 5,267,997 A | 12/1993 | Farin et al. |
| 5,267,998 A | 12/1993 | Hagen |
| 5,269,780 A | 12/1993 | Roos |
| 5,269,782 A | 12/1993 | Sutter |
| 5,273,524 A | 12/1993 | Fox et al. |
| 5,277,696 A | 1/1994 | Hagen |
| 5,281,216 A | 1/1994 | Klicek |
| 5,282,799 A | 2/1994 | Rydell |
| 5,290,287 A | 3/1994 | Boebel et al. |
| 5,295,990 A | 3/1994 | Levin |
| 5,300,087 A | 4/1994 | Knoepfler |
| 5,304,124 A | 4/1994 | Essig et al. |
| 5,305,121 A | 4/1994 | Moll |
| 5,308,311 A | 5/1994 | Eggers et al. |
| 5,318,564 A | 6/1994 | Eggers |
| 5,320,627 A | 6/1994 | Sorensen et al. |
| 5,322,055 A | 6/1994 | Davison et al. |
| 5,324,289 A | 6/1994 | Eggers |
| 5,330,471 A | 7/1994 | Eggers |
| 5,342,359 A | 8/1994 | Rydell |
| 5,342,381 A | 8/1994 | Tidemand |
| 5,344,420 A | 9/1994 | Hilal et al. |
| 5,352,222 A | 10/1994 | Rydell |
| 5,352,235 A | 10/1994 | Koros et al. |
| 5,356,408 A | 10/1994 | Rydell |
| 5,366,476 A | 11/1994 | Noda |
| 5,368,015 A | 11/1994 | Wilk |
| 5,383,874 A | 1/1995 | Jackson et al. |

(56) References Cited

U.S. PATENT DOCUMENTS

| | | |
|---|---|---|
| 5,383,876 A | 1/1995 | Nardella |
| 5,383,880 A | 1/1995 | Hooven |
| 5,387,196 A | 2/1995 | Green et al. |
| 5,391,166 A | 2/1995 | Eggers |
| 5,395,369 A | 3/1995 | McBrayer et al. |
| 5,396,900 A | 3/1995 | Slater et al. |
| 5,403,312 A | 4/1995 | Yates et al. |
| 5,409,487 A | 4/1995 | Jalbert et al. |
| 5,417,687 A | 5/1995 | Nardella et al. |
| 5,423,814 A | 6/1995 | Zhu et al. |
| 5,443,463 A | 8/1995 | Stern et al. |
| 5,445,638 A | 8/1995 | Rydell et al. |
| 5,451,224 A | 9/1995 | Goble et al. |
| 5,456,684 A | 10/1995 | Schmidt et al. |
| 5,460,182 A | 10/1995 | Goodman et al. |
| 5,462,546 A | 10/1995 | Rydell |
| 5,464,404 A | 11/1995 | Abela et al. |
| 5,482,054 A | 1/1996 | Slater et al. |
| 5,484,435 A | 1/1996 | Fleenor et al. |
| 5,484,436 A | 1/1996 | Eggers et al. |
| 5,496,312 A | 3/1996 | Klicek |
| 5,496,317 A | 3/1996 | Goble et al. |
| 5,514,134 A | 5/1996 | Rydell et al. |
| 5,527,313 A | 6/1996 | Scott et al. |
| 5,531,744 A | 7/1996 | Nardella et al. |
| 5,540,684 A | 7/1996 | Hassler, Jr. |
| 5,540,685 A | 7/1996 | Parins et al. |
| 5,542,916 A | 8/1996 | Hirsch et al. |
| 5,542,945 A | 8/1996 | Fritzsch |
| 5,549,606 A | 8/1996 | McBrayer et al. |
| 5,558,100 A | 9/1996 | Cox |
| 5,558,671 A | 9/1996 | Yates |
| 5,569,243 A | 10/1996 | Kortenbach et al. |
| 5,571,100 A | 11/1996 | Goble et al. |
| 5,573,534 A | 11/1996 | Stone |
| 5,573,535 A | 11/1996 | Viklund |
| 5,599,347 A | 2/1997 | Hart et al. |
| 5,599,350 A | 2/1997 | Schulze et al. |
| 5,603,711 A | 2/1997 | Parins et al. |
| 5,609,560 A | 3/1997 | Ichikawa et al. |
| 5,611,803 A | 3/1997 | Heaven et al. |
| 5,624,452 A | 4/1997 | Yates |
| 5,626,578 A | 5/1997 | Tihon |
| 5,637,110 A | 6/1997 | Pennybacker et al. |
| 5,651,780 A | 7/1997 | Jackson et al. |
| 5,658,281 A | 8/1997 | Heard |
| 5,665,085 A | 9/1997 | Nardella |
| 5,665,100 A | 9/1997 | Yoon |
| 5,667,526 A | 9/1997 | Levin |
| 5,669,907 A | 9/1997 | Platt, Jr. et al. |
| 5,674,184 A | 10/1997 | Hassler, Jr. |
| 5,674,220 A | 10/1997 | Fox et al. |
| 5,681,282 A | 10/1997 | Eggers et al. |
| 5,683,385 A | 11/1997 | Kortenbach et al. |
| 5,683,388 A | 11/1997 | Slater |
| 5,688,269 A | 11/1997 | Newton et al. |
| 5,688,270 A | 11/1997 | Yates et al. |
| 5,693,051 A | 12/1997 | Schulze et al. |
| 5,697,949 A | 12/1997 | Giurtino et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,713,896 A | 2/1998 | Nardella |
| 5,718,703 A | 2/1998 | Chin |
| 5,733,283 A | 3/1998 | Malis et al. |
| 5,735,848 A | 4/1998 | Yates et al. |
| 5,735,849 A | 4/1998 | Baden et al. |
| 5,743,906 A | 4/1998 | Parins et al. |
| 5,749,893 A | 5/1998 | Vidal et al. |
| 5,755,717 A | 5/1998 | Yates et al. |
| 5,810,811 A | 9/1998 | Yates et al. |
| 5,833,690 A | 11/1998 | Yates et al. |
| 5,852,238 A | 12/1998 | Vaitkus |
| 5,891,142 A | 4/1999 | Eggers et al. |
| 5,893,835 A * | 4/1999 | Witt ............... A61B 17/320092 601/2 |
| 5,920,390 A | 7/1999 | Farahi et al. |
| 5,925,055 A | 7/1999 | Adrian et al. |
| 5,931,848 A | 8/1999 | Saadat |
| 5,935,143 A | 8/1999 | Hood |
| 5,951,549 A | 9/1999 | Richardson et al. |
| 5,957,882 A | 9/1999 | Nita et al. |
| 5,964,758 A | 10/1999 | Dresden |
| 5,968,060 A | 10/1999 | Kellogg |
| 5,984,919 A | 11/1999 | Hilal et al. |
| 5,989,274 A | 11/1999 | Davison et al. |
| 5,993,378 A | 11/1999 | Lemelson |
| 6,004,335 A | 12/1999 | Vaitekunas et al. |
| 6,010,512 A | 1/2000 | Chu et al. |
| 6,015,969 A | 1/2000 | Nathel et al. |
| 6,024,741 A | 2/2000 | Williamson, IV et al. |
| 6,027,515 A | 2/2000 | Cimino |
| 6,030,384 A | 2/2000 | Nezhat |
| 6,056,735 A | 5/2000 | Okada et al. |
| 6,068,647 A | 5/2000 | Witt et al. |
| 6,069,689 A | 5/2000 | Zeng et al. |
| 6,077,285 A | 6/2000 | Boukhny |
| 6,083,191 A | 7/2000 | Rose |
| 6,090,120 A | 7/2000 | Wright et al. |
| 6,096,033 A | 8/2000 | Tu et al. |
| 6,099,537 A | 8/2000 | Sugai et al. |
| 6,110,188 A | 8/2000 | Narciso, Jr. |
| 6,117,152 A | 9/2000 | Huitema |
| 6,124,597 A | 9/2000 | Shehada et al. |
| 6,134,003 A | 10/2000 | Tearney et al. |
| 6,139,561 A | 10/2000 | Shibata et al. |
| 6,159,196 A | 12/2000 | Ruiz |
| 6,159,225 A | 12/2000 | Makower |
| 6,162,220 A | 12/2000 | Nezhat |
| 6,162,235 A | 12/2000 | Vaitekunas |
| 6,165,191 A | 12/2000 | Shibata et al. |
| 6,174,324 B1 | 1/2001 | Egan et al. |
| 6,179,837 B1 | 1/2001 | Hooven |
| 6,217,591 B1 | 4/2001 | Egan et al. |
| 6,231,587 B1 | 5/2001 | Makower |
| 6,237,605 B1 | 5/2001 | Vaska et al. |
| 6,238,386 B1 | 5/2001 | Muller et al. |
| 6,240,305 B1 | 5/2001 | Tsuchiya |
| 6,241,692 B1 | 6/2001 | Tu et al. |
| 6,251,110 B1 | 6/2001 | Wampler |
| 6,334,860 B1 | 1/2002 | Dorn |
| 6,361,534 B1 | 3/2002 | Chen et al. |
| 6,436,920 B1 | 8/2002 | Fujimura et al. |
| 6,494,897 B2 | 12/2002 | Sterman et al. |
| 6,582,451 B1 | 6/2003 | Marucci et al. |
| 6,648,883 B2 | 11/2003 | Francischelli et al. |
| 6,656,175 B2 | 12/2003 | Francischelli et al. |
| 6,663,627 B2 | 12/2003 | Francischelli et al. |
| 6,689,128 B2 | 2/2004 | Sliwa, Jr. et al. |
| 6,701,931 B2 | 3/2004 | Sliwa, Jr. et al. |
| 6,723,092 B2 | 4/2004 | Brown et al. |
| 6,786,905 B2 | 9/2004 | Swanson et al. |
| 6,913,600 B2 | 7/2005 | Valley et al. |
| 6,926,712 B2 | 8/2005 | Phan |
| 6,989,010 B2 | 1/2006 | Francischelli et al. |
| 7,029,470 B2 | 4/2006 | Francischelli et al. |
| 8,226,675 B2 * | 7/2012 | Houser .......... A61B 17/320068 606/169 |
| 8,292,888 B2 | 10/2012 | Whitman |
| 8,845,665 B2 | 9/2014 | Whitman |
| 2002/0017306 A1 | 2/2002 | Cox et al. |
| 2002/0128639 A1 | 9/2002 | Pless et al. |

FOREIGN PATENT DOCUMENTS

| | | |
|---|---|---|
| EP | 0572131 A1 | 12/1993 |
| EP | 0598579 A1 | 5/1994 |
| EP | 0653922 A1 | 5/1995 |
| EP | 0878169 A1 | 11/1998 |
| EP | 0717966 B1 | 4/2003 |
| FR | 598149 A | 12/1925 |
| FR | 2355521 A1 | 1/1978 |
| FR | 2647683 A1 | 12/1990 |

(56) References Cited

FOREIGN PATENT DOCUMENTS

| | | | |
|---|---|---|---|
| GB | 1546624 | A | 5/1979 |
| GB | 2037167 | A | 7/1980 |
| GB | 2066104 | A | 7/1981 |
| GB | 2128881 | A | 5/1984 |
| GB | 2133290 | A | 7/1984 |
| WO | 9308754 | A1 | 5/1993 |
| WO | 9717033 | A2 | 5/1997 |
| WO | 0000992 | A2 | 1/2000 |
| WO | 0110291 | A1 | 2/2001 |
| WO | 01/17448 | | 3/2001 |
| WO | 02058539 | A2 | 8/2002 |

OTHER PUBLICATIONS

D. Lang Stevenson, "Combined Biathermy Forceps and Scissors", The Lancet, Oct. 1959.
S. L. Corson, M.D., "Two New Laparoscopic Instruments: Bipolar Sterilizing Forceps and Uterine Manipulator", Journal of Association for the Advancement of Medical Instrumentation, Jan. 1977.

\* cited by examiner

BIPOLAR OR ULTRASONIC SURGICAL DEVICE

CROSS-REFERENCES TO RELATED APPLICATIONS

This application is a continuation application claiming the benefit of and priority to U.S. patent application Ser. No. 13/967,441, filed on Aug. 15, 2013, now U.S. Pat. No. 8,845,665, which is a continuation application claiming the benefit of and priority to U.S. patent application Ser. No. 13/611,273, filed on Sep. 12, 2012, now U.S. Pat. No. 8,523,890, which is a divisional application claiming the benefit of and priority to U.S. patent application Ser. No. 10/128,768, filed on Apr. 22, 2002, now U.S. Pat. No. 8,292,888, which claims the benefit of and priority to U.S. Provisional Patent Application Ser. No. 60/285,113, filed on Apr. 20, 2001, and U.S. Provisional Patent Application Ser. No. 60/289,370, filed on May 8, 2001, each of which is expressly incorporated herein in its entirety by reference thereto.

U.S. patent application Ser. No. 10/128,768 also expressly incorporates in its entirety by reference thereto International Published Patent Application No. WO 00/72765, filed on Jun. 2, 2000. U.S. patent application Ser. No. 10/128,768 also expressly incorporates in its entirety by reference thereto U.S. patent application Ser. No. 09/723,715, filed on Nov. 28, 2000, now U.S. Pat. No. 6,793,652, issued on Sep. 21, 2004, which is a continuation-in-part of U.S. patent application Ser. No. 09/324,451, filed on Jun. 2, 1999, now U.S. Pat. No. 6,315,184, issued on Nov. 13, 2001, which is a continuation-in-part of U.S. patent application Ser. No. 09/324,452, filed on Jun. 2, 1999, now U.S. Pat. No. 6,443,973, issued on Sep. 3, 2002, which is a continuation-in-part of U.S. patent application Ser. No. 09/351,534, filed on Jul. 12, 1999, now U.S. Pat. No. 6,264,087, issued on Jul. 24, 2001, which is a continuation-in-part of U.S. patent application Ser. No. 09/510,923, filed on Feb. 22, 2000, now U.S. Pat. No. 6,517,565, issued on Feb. 11, 2003, which is a continuation-in-part of U.S. patent application Ser. No. 09/510,927, filed on Feb. 22, 2000, now U.S. Pat. No. 6,716,233, issued on Apr. 6, 2004, which is a continuation-in-part of U.S. patent application Ser. No. 09/324,452, filed on Jun. 2, 1999, now U.S. Pat. No. 6,443,973, issued on Sep. 3, 2002, which is a continuation-in-part of U.S. patent application Ser. No. 09/510,932, filed on Feb. 22, 2000, now U.S. Pat. No. 6,491,201, issued on Dec. 10, 2002, each of which is expressly incorporated in U.S. patent application Ser. No. 10/128,768 in its entirety by reference thereto.

FIELD OF THE INVENTION

The present invention relates to a bipolar and/or ultrasonic surgical device.

BACKGROUND INFORMATION

Various bipolar, ultrasonic, and/or electro-mechanical surgical devices exist which are used to cauterize and coagulate tissue in a surgical procedure. Some devices use bipolar electrical energy in order to cut and/or coagulate tissue. Generally, bipolar surgical instruments clamp the tissue prior to the application of the electro surgical energy. Some devices provide opposing jaws to perform the clamping or grasping procedure where an electrode(s) is disposed on the inner surface of the jaws. These bipolar surgical instruments coagulate, cut and separate tissue by charging the electrode(s) to apply heat to the tissue between the jaws.

During the use of bipolar surgical instruments, the heat generated by the electrodes causes the desired coagulation and cutting of tissue. Several of the bipolar surgical instruments may encounter problems with the application of the heat of the tissue. Adjacent tissue may be damaged due to application of excessive heat. Conversely, where less energy is applied to the electrodes in order to prevent over heating, the coagulation of the tissue may require more time than desired.

Fully mechanical surgical devices are also available in order to perform the above procedure. The mechanical devices require the application of force to staple and cut the tissue. Many of the existing mechanical devices use four rows of staples in order to ensure the proper results. Due to the cutting and stapling functions, many of these mechanical surgical instruments require an excessive amount of force in order to effectively perform their functions.

Therefore, an object of the present invention provides an electro-mechanical that allows greater control of heat applied to the tissue by the bipolar electrodes and allows the use of less mechanical force when incorporating the use of mechanical force.

SUMMARY

The above and other beneficial objects and advantages of the present invention may be effectively attained by providing a bipolar, ultrasonic and/or electro-mechanical surgical device as described herein.

In an example embodiment and/or example method, the present invention provides for an electro-mechanical surgical device including a housing, at least two opposing jaw, and at least one electrical contact associated with at least one of the jaws. In a further example embodiment of the present invention, the electrical contact is at least one of a bipolar electrical contact and an ultrasonic electrical contact.

In a further example embodiment and/or example method of the present invention, the surgical device includes a row of electrical contacts associated with the at least one of the opposing jaws. In a further example embodiment and/or example method of the present invention, the surgical device includes at least two rows of electrical contacts associated with at least one of the opposing jaws.

In a further example embodiment and/or example method of the present invention, the surgical device includes a sensor configured and arranged to sense temperature of tissue disposed between the upper jaw and the lower jaw. In a further example embodiment and/or example method of the present invention, the sensor may be configured to transmit a signal to the surgical device via, e.g., a data transfer cable, the signal indicating the temperature of the tissue disposed between the upper jaw and the lower jaw. Further, the signal transmitted by the sensor may effect a movement of the jaw(s) and/or a change in the heating effect of the electrode(s) on the tissue.

In a further example embodiment and/or example method of the present invention, the surgical device includes, on at least one of the jaws, at least one pierceable ampulla containing fluid so that the fluid is releasable when the upper jaw and the lower jaw are in the closed position and so that the electrode passes through the tissue disposed between the upper jaw and the lower jaw into the at least one pierceable ampulla. That fluid may include, for example, a variety of fluids or matters or dyes, for example, collagen, fibrin, dye, matter configured to effect anastomosis, matter configured to seal tissue and matter configured to effect hemostasis, etc. In a further example embodiment and/or example method of the present invention, the electrode and/or row(s) of electrodes may be activated so that the tissue is coagulated to induce hemostasis.

In a further example embodiment and/or example method of the present invention, an electro-mechanical surgical system may include a surgical device and a surgical instrument. The surgical device may include a housing, an elongated shaft extending from the housing, a distal end of the elongated shaft configured to detachably couple with a surgical instrument, a steering arrangement, the steering arrangement configured to steer the distal end of the elongated shaft, and a motor system disposed within the housing, the motor system configured to drive the drive shafts and the steering arrangement. The surgical instrument may include an upper jaw, a lower jaw, the lower jaw opposing the upper jaw and the lower jaw configured to detachably couple with the distal end of the elongated shaft of the surgical device, and an electrode or row(s) of electrodes provided on at least one of the lower jaw and the upper jaw. The electrode(s) may be associated with any one of more of the jaws, such as, for example, the inner surface of an upper jaw of two opposing jaws.

In a further example embodiment and/or example method of the present invention, one of the opposing jaws, e.g., the lower jaw, includes at least two rows of staples and a cutting device.

In further example embodiments and/or example methods of the present invention, there may be a reduced number of staples and thus less mechanical force to form staples and transect tissue. Further, example embodiments and/or example methods may use bipolar radio-frequency (RF) energy and/or staples to coagulate and cut tissue. Further, example embodiments and/or example methods may include one row of staples or no staples. Further, example embodiments may include an energy surgical attachment (DLU) which consists of two opposing jaws where the two opposing jaws may include, e.g., one or two, rows of bipolar electrical contacts.

BRIEF DESCRIPTION OF THE DRAWINGS

FIG. 1b is a detailed view of the interior of a flexible shaft of the electro-mechanical surgical device illustrated in FIG. 1a.

DETAILED DESCRIPTION

Figure 1A:
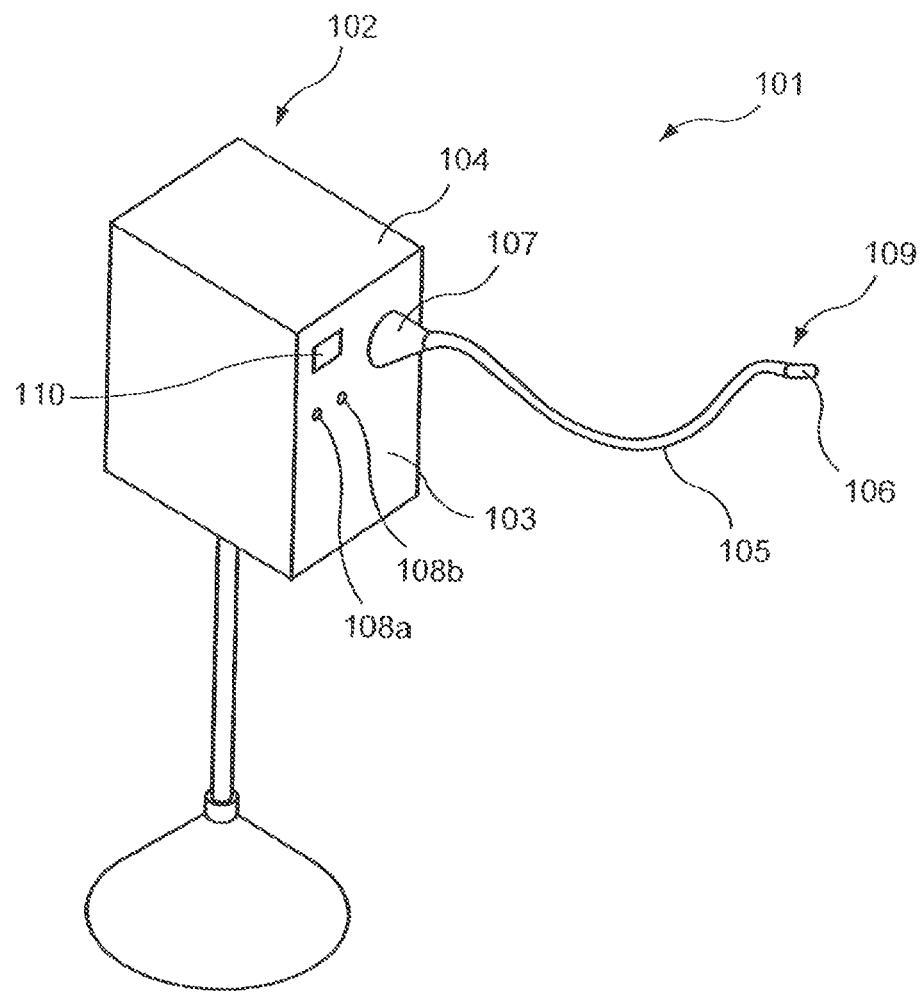
FIG. 1a is a perspective view of an electro-mechanical driver device, which may be coupled to the surgical device according to the present invention.

Referring to FIG. 1a, a perspective view of an electro-mechanical driver device 101 according to one example embodiment of the present invention is illustrated. Such an electro-mechanical driver device is described in, for example, U.S. patent application Ser. No. 09/723,715, entitled "Electro-Mechanical Surgical Device," now U.S. Pat. No. 6,793,652, which is expressly incorporated herein in its entirety by reference thereto. Electro-mechanical driver device 101 may include, for example, a remote power console 102, which includes a housing 104 having a front panel 103. Mounted on front panel 103 are a display device 106 and indicators 108a and 108b. A flexible shaft 105 may extend from housing 104 and may be detachably secured thereto via a first coupling 107. The distal end 109 of flexible shaft 105 may include a second coupling 106 adapted to detachably secure a surgical instrument or attachment to the distal end 109 of the flexible shaft 105. In accordance with the example embodiment of the present invention, the surgical instrument or attachment may be, for example, a surgical stapler and cutter device that utilizes electrical energy to cut and/or coagulate tissue. Other surgical instruments are described, for example, in U.S. patent application Ser. No. 09/324,451, entitled "Stapling Device for Use with an Electromechanical Driver Device for Use with Anastomosing, Stapling, and Resecting Instruments," now U.S. Pat. No. 6,315,184, U.S. patent application Ser. No. 09/324,452, entitled "Electromechanical Driver Device for Use with Anastomosing, Stapling, and Resecting Instruments," now U.S. Pat. No. 6,443,973, U.S. patent application Ser. No. 09/351,534, entitled "Expanding Parallel Jaw Device For Use With An Electromechanical Driver Device," now U.S. Pat. No. 6,264,087, U.S. patent application Ser. No. 09/510,926, entitled "Vessel and Lumen Expander Attachment for Use with an Electromechanical Driver Device," now U.S. Pat. No. 6,348,061, U.S. patent application Ser. No. 09/510,927, entitled "Electromechanical Driver and Remote Surgical Instrument Attachment Having Computer Assisted Control Capabilities," now U.S. Pat. No. 6,716,233, U.S. patent application Ser. No. 09/510,931, entitled "Tissue Stapling Attachment for Use with an Electromechanical Driver Device," now U.S. Pat. No. 6,533,157, U.S. patent application Ser. No. 09/510,932, entitled "Fluid Delivery Mechanism for Use with Anastomosing, Stapling, and Resecting Instruments," now U.S. Pat. No. 6,491,201, and U.S. patent application Ser. No. 09/510,933, entitled "Fluid Delivery Device for Use with Anastomosing, Resecting and Stapling Instruments," now U.S. Pat. No. 6,488,197, each of which is expressly incorporated herein in its entirety by reference thereto.

According to a further example embodiment, flexible shaft 105 may include a tubular outer sheath, which may include a coating or other sealing arrangement to provide a fluid-tight seal between the interior channel thereof and the environment. The sheath may be formed of a tissue-compatible, sterilizable elastomeric material. The sheath may also be formed of a material that is autoclavable. An example embodiment of such a flexible shaft is described, for example, in U.S. patent application Ser. No. 10/099,634, entitled "Moisture-Detecting Shaft For Use With An Electro-Mechanical Surgical Device," now U.S. Pat. No. 7,951,071, which is expressly incorporated herein in its entirety by reference thereto.

Figure 1B:
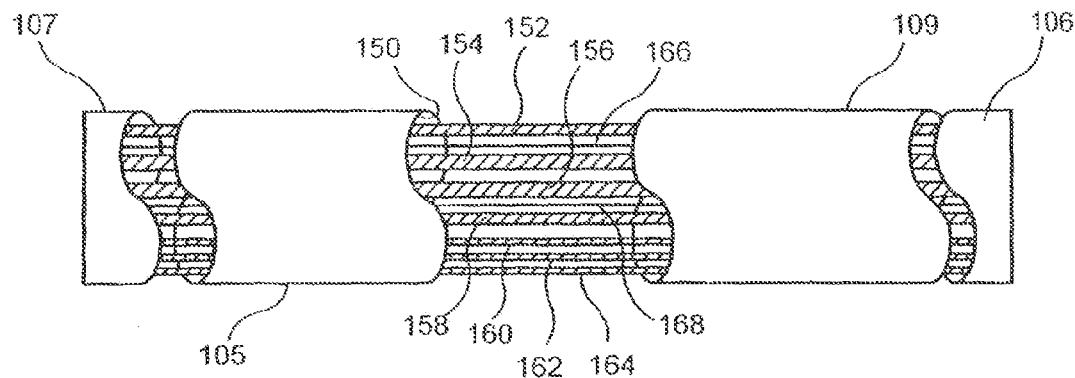

As illustrated in FIG. 1b, disposed within the interior channel 150 of the flexible shaft 105, and extending along the length thereof, may be a first rotatable drive shaft 152, a second rotatable drive shaft 154, a first steering cable 156, a second steering cable 158, a third steering cable 160, a fourth steering cable 162, one or more data transfer cables 164, and/or two leads 166 and 168, all terminating at the second coupling 106, at the distal end 109 of the flexible shaft 105. The leads 166 and 168 may be provided to, for example, transmit current to and/or from an attached surgical instrument or attachment. The remote power console 102 may include a motor system, which includes one or more motors configured to rotate the first and second rotatable drive shafts 152, 154 and to apply tension or otherwise drive the steering cables to thereby steer the distal end 109 of the flexible shaft 105. An example embodiment of a motor arrangement is described, for example, in U.S. patent application Ser. No. 09/510,923, entitled "Carriage Assembly For Controlling A Steering Wire Steering Mechanism Within A Flexible Shaft," now U.S. Pat. No. 6,517,565, which is expressly incorporated herein in its entirety by reference thereto.

Figure 1C:
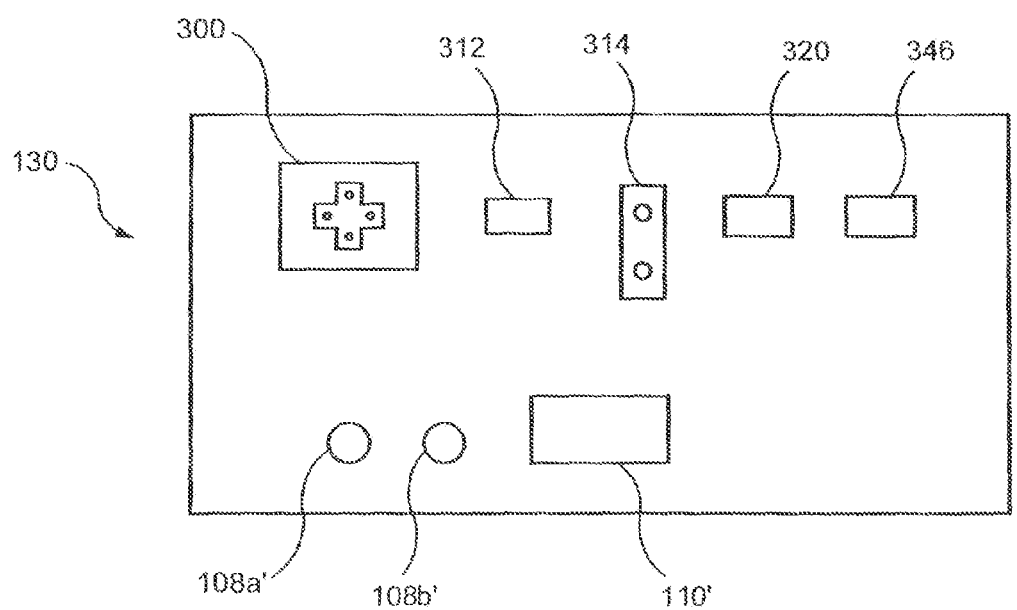
FIG. 1c is a schematic top view of a remote control unit of the electro-mechanical surgical device.

Referring to FIG. 1c, there is shown a top schematic view of a remote control unit ("RCU") 130 for remotely controlling the electro-mechanical driver device 101 illustrated in FIG. 1a. The RCU 130 may be, for example, a wired remote control unit, a wireless remote control unit, a hybrid remote control unit, etc. The RCU 130 may include a number of operable control elements 300, 312, 314, 320 and 346 which may be, for example, toggle switches, button switches, analog switches, control knobs, potentiometers, etc. The RCU 130 may also include indicators 108a', 108b' and a display device 110'. Although FIG. 1c illustrates five control elements 300, 312, 314, 320 and 346, any appropriate number of control elements may be provided. In a further example embodiment of the present invention, RCU 130 may be configured to clamp onto the sheath of the flexible shaft 105.

Figure 1D:
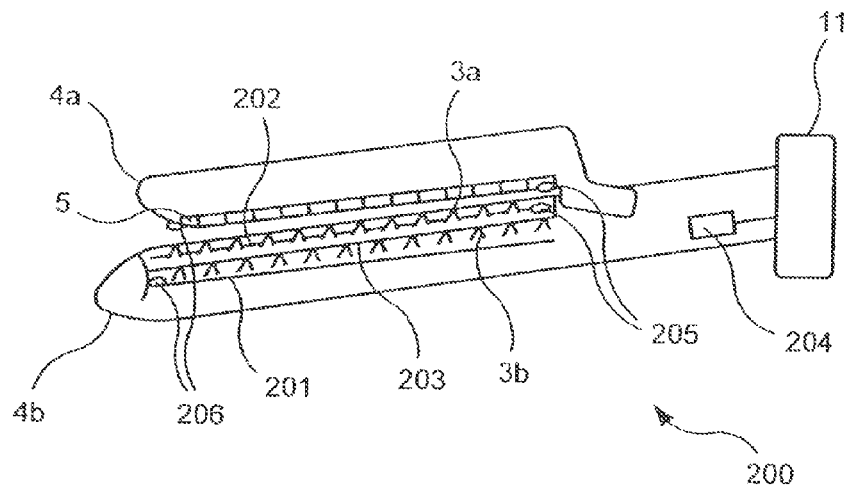
FIG. 1d is a perspective view of a surgical device according to one embodiment of the present invention.

Referring to FIG. 1d, there is illustrated a perspective view of a further example embodiment of the surgical device according to the present invention. The surgical device 200 may be used in combination with the electro-mechanical driver device 101 illustrated in FIG. 1a. The surgical device 200 may also be used in combination with a manually-operable driver device.

The surgical device 200 according to the example embodiment includes a coupling 11 adapted and configured to detachably couple the surgical device 200 with the second coupling device 106 of the flexible shaft 105 of the driver device 101 illustrated in FIG. 1a. The couplings 11, 106 may include a quick-connect type fitting, such as a rotary quick-connect type fitting, a bayonet type fitting, etc. The couplings 11 and 106 may also be threaded couplings. In an alternative example embodiment, the surgical device 200 is permanently connected to or integral with the driver device, electro-mechanical or manual, for example.

The surgical device 200 includes an upper jaw 4a and a lower jaw 4b. In the example embodiment illustrated in FIG. 1d, the lower jaw 4b is connected to coupling 11.

Electrodes 3a, 3b may be provided on an inner surface of lower jaw 4b. In alternative example embodiments, electrodes may be provided on the upper jaw 4a, or on both the upper jaw 4a and the lower jaw 4b. In this alternative example embodiment, the lower jaw 4b may also include two rows of staples 201, 202 and a cutting device 203.

The surgical device 200 may also include sensors 205, 206. These sensors may be configured and arranged to, for example, sense the temperature of tissue disposed between jaws 4a and 4b. When coupled to the driver device 101 of FIG. 1a, for example, signals from the sensors 205, 206 may be transmitted to the driver device, e.g., via data transfer cables.

The upper jaw 4a illustrated in FIG. 1d may include pierceable ampullae 5, which may contain fluid or matter to induce hemostasis. The fluid may include, for example, collagen, fibrin, etc. The use of other fluids or matters is, of course, possible. This fluid or matter, for example, collagen, fibrin, dye, matter configured to effect anastomosis, matter configured to seal tissue and matter configured to effect hemostasis, etc. may be released when the jaws 4a, 4b are closed and the electrodes 3a, 3b pass through the tissue and into the ampullae 5, releasing the fluid or matter. Simultaneously, the electrodes 3a, 3b are activated and tissue may be coagulated to induce hemostasis. Sensors 205, 206 monitor the amount of heat provided and duration of application. While the current passes between the electrodes 3a, 3b, a driver may advance to eject two rows of staples 201, 202 on either side of the cutting device 203. In a further example embodiment, the stapling mechanism includes a replaceable tray or cartridge of open staples set within the lower jaw 4*b* and a set of corresponding staple guides within the upper jaw 4*a*, such that when the surgical device 200 is in a closed position, the open staples are arranged to oppose the corresponding staple guides. The stapling mechanism may also include a wedge pushing system whereby once the linear clamping mechanism is in a closed position, a wedge arranged in a channel below the tray of open staples is pushed through the channel. As the wedge moves through the channel, a sloping surface of the wedge pushes the open staples against the corresponding staple guides, thereby closing the staples. After the staples have been closed, the wedge is pulled back through the channel. The second drive extension pushes or pulls the wedge through the channel, depending on the turning direction of the corresponding motor in the, for example, electro-mechanical driver device, by engaging a threaded horizontal shaft upon which the wedge, having a matching inner thread, rides. An example embodiment of such a stapling device is described, for example, in U.S. patent application Ser. No. 09/324,451, entitled "Stapling Device For Use With An Electromechanical Driver Device For Use With Anastomosing, Stapling, and Resecting Instruments," now U.S. Pat. No. 6,315,184, and in U.S. patent application Ser. No. 09/999,546, entitled "Surgical Device", now U.S. Pat. No. 7,695,485, each of which is expressly incorporated herein in its entirety by reference thereto.

In a further example embodiment of the present invention, the surgical device 200 includes a memory device 204. The memory device 204 may be, for example, a read-only memory, a programmable memory, a random access memory, etc. The memory device 204 may be configured and arranged to store, for example, a unique serial number of the surgical device 200, and/or a device type indication. The memory device 204 may also be configured and arranged to store counter data indicating how may times the surgical device 200 has been used. When coupled to the driver device 101 illustrated in FIG. 1*a*, for example, this memory device 204 may be read by the driver device 101, e.g., via a data transfer cable. In operation, the surgical device 200 is first connected to the electro-mechanical driver device 101 illustrated in FIG. 1*a* via coupling 11. A driver device may read the memory device 204 to determine, for example, the device type, so that the driver device may execute the movements of the surgical device 200 in a suitable fashion.

Figure 1E:
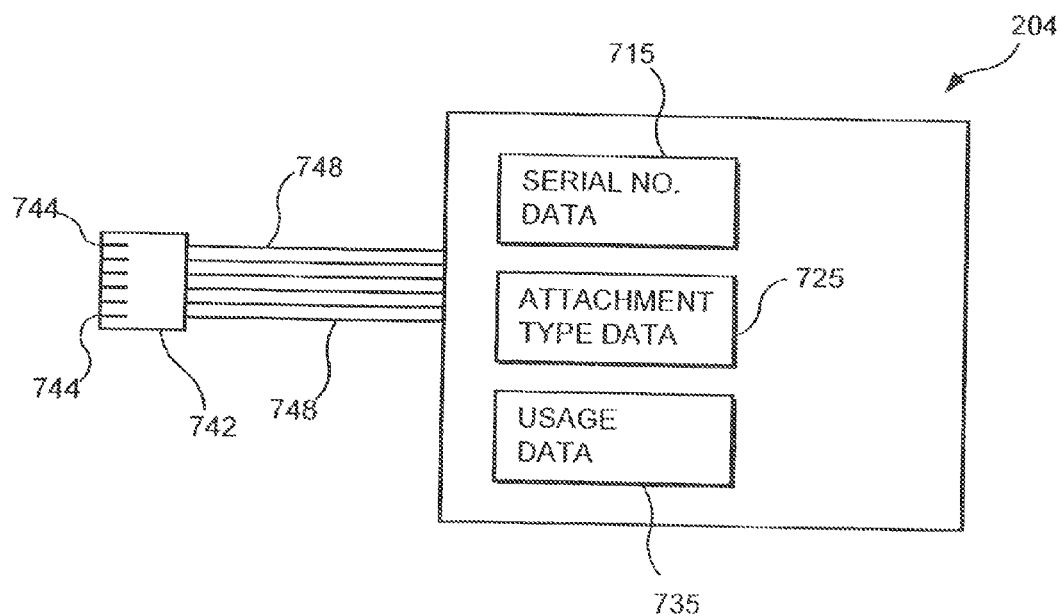
FIG. 1e is an example embodiment of a memory device according to the present invention.

FIG. 1*e* is a schematic view of memory unit 204. As illustrated, data connector 742 includes contacts 744, each electrically and logically connected to memory unit 204 via a respective line 748. Memory unit 204 is configured to store, for example, a serial number data 715, an attachment type identifier (ID) data 725 and a usage data 735. Memory unit 204 may additionally store other data. Both the serial number data 715 and the ID data 725 may be configured as read-only data. In the example embodiment, serial number data 715 is data uniquely identifying the particular surgical instrument or attachment, whereas the ID data 725 is data identifying the type of the attachment, such as, for example, a bipolar surgical device, an ultrasonic surgical device, a circular surgical stapler attachment, a linear surgical stapler attachment, etc. The usage data 735 represents usage of the particular attachment, such as, for example, the number of times that jaws 4*a*, 4*b* of surgical device 200 have been actuated.

Each type of surgical instrument or attachment attachable to the distal end 109 of the flexible shaft 105 may be designed and configured to be used a single time or multiple times. The surgical instrument or attachment may also be designed and configured to be used a predetermined number of times. Accordingly, the usage data 735 may be used to determine whether the surgical instrument or attachment has been used and whether the number of uses has exceeded the maximum number of permitted uses. In a further example embodiment, an attempt to use a surgical instrument or attachment after the maximum number of permitted uses has been reached may generate an ERROR condition.

A controller within the electro-mechanical device 101, for example, as illustrated in FIG. 1*a*, may be configured to execute an operating program or algorithm based on the read ID data 725. Such a controller is described, for example, in U.S. patent application Ser. No. 09/723,715, entitled "Electro-Mechanical Surgical Device", now U.S. Pat. No. 6,793,652, and U.S. patent application Ser. No. 09/836,781 entitled "Electro-Mechanical Surgical Device," now U.S. Pat. No. 6,981,941, each of which is expressly incorporated herein in its entirety by reference thereto. The remote power console 102, for example, as illustrated in FIG. 1*a*, may include a memory unit which may be configured to store the operating programs or algorithms for each available type of surgical instrument or attachment, the controller selects and/or reads the operating program or algorithm from the memory unit in accordance with the ID data 725 read from the memory unit 204 of an attached surgical instrument or attachment. The operating programs or algorithms stored in the memory unit may be updated, added, deleted, improved or otherwise revised as necessary. In a further example embodiment, the serial number data 715 and/or usage data 735 may also be used to determine which of a plurality of operating programs or algorithms is read or selected from the memory unit. In a further example embodiment, the operating program or algorithm may alternatively be stored in the memory unit 204 of the surgical instrument or attachment and transferred to the controller via the data transfer cables 164. Once the appropriate operating program or algorithm is read or selected by, or transmitted to, the controller, the controller may cause the operating program or algorithm to be executed in accordance with operations performed by the user, e.g., via the RCU 130. The controller may be electrically and logically connected with one or more motors arranged in the remote power console 102, for example, as illustrated in FIG. 1*a*, and may be configured to control these motors in accordance with the read, selected or transmitted operating program or algorithm.

According to a further example embodiment of the present invention, surgical device 200 includes a system configured to open and close the jaws 4*a*, 4*b* relative to one another, and a system configured to drive the staples 201, 202 and to drive the cutting device 203. Examples of such systems are described in detail in U.S. patent application Ser. No. 09/324,421, entitled "Alignment Device And Lithographic Apparatus Comprising Such A Device," now U.S. Pat. No. 6,417,922, U.S. patent application Ser. No. 09/324,451, entitled "Stapling Device For Use With An Electromechanical Driver Device For Use With Anastomosing, Stapling, and Resecting Instruments," now U.S. Pat. No. 6,315,184, U.S. patent application Ser. No. 09/351,534, entitled "Expanding Parallel Jaw Device For Use With An Electromechanical Driver Device," now U.S. Pat. No. 6,264,087, each of which is expressly incorporated herein in its entirety by reference thereto.

Figure 1F:
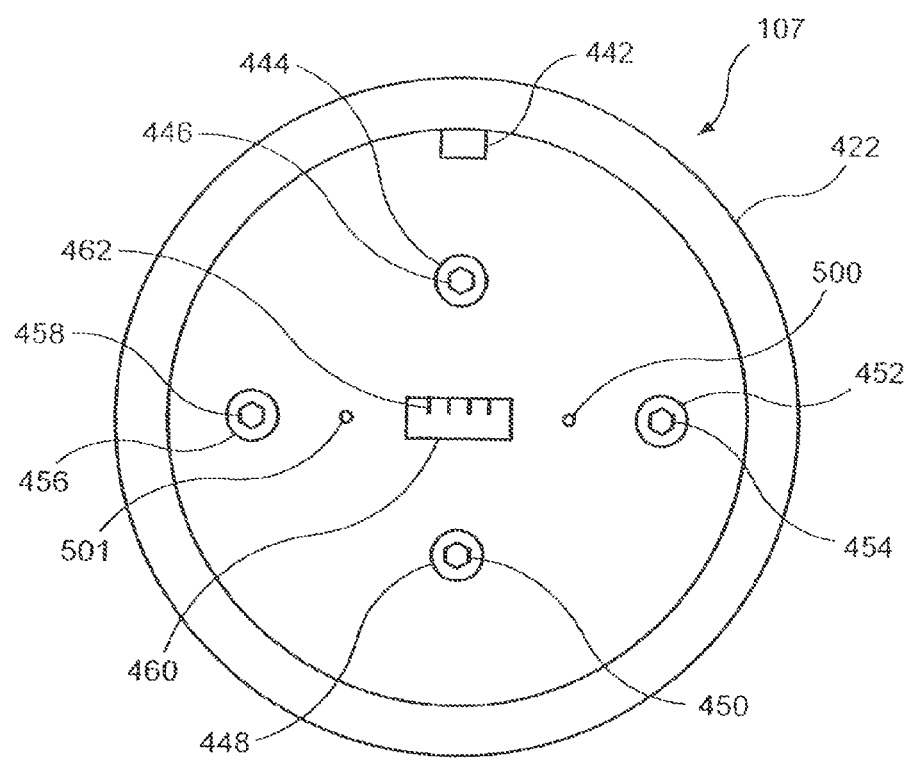
FIG. 1f is an end view of an example embodiment of a coupling.

FIG. 1*f* is an end view of an example embodiment of coupling 107 illustrated in FIG. 1*a*. The coupling 107 includes a first connector 444, a second connector 448, a third connector 452 and a fourth connector 456, each rotatably secured to the coupling 107. Each of the connectors 444, 448, 452 and 456 includes a respective recess 446, 450, 454 and 458. As illustrated in FIG. 1*f*, each recess 446, 450, 454 and 458 may be hexagonally shaped. It should be appreciated, however, that the recesses 446, 450, 454 and 458 may have any shape and configuration to non-rotatably couple and rigidly attach the connectors 444, 448, 452, 456 to respective drive shafts of a motor arrangement contained within driver device 101 illustrated in FIG. 1*a*. Complementary projections may be provided on respective drive shafts of the motor arrangement to thereby drive the drive elements of the flexible shaft 105. It should also be appreciated that the recesses may be provided on the drive shafts and complementary projections may be provided on the connectors 444, 448, 452, 456. Any other coupling arrangement configured to non-rotatably and releasably couple the connectors 444, 448, 452, 456 and the drive shafts of the motor arrangement may be provided. Coupling 107 also includes contacts 500, 501 configured to transfer additional voltage from the remote power console 102 through flexible shaft 105.

One of the connectors 444, 448, 452, 456 is non-rotatably secured to the first drive shaft 152, and another one of the connectors 444, 448, 452, 456 is non-rotatably secured to the second drive shaft 154. The remaining two of the connectors engage with transmission elements configured to apply tensile forces on the steering cables 156, 158, 160 and 162 to thereby steer the distal end 109 of the flexible shaft 205. The data transfer cable 164 is electrically and logically connected with data connector 460. Data connector 460 includes, for example, electrical contacts 462, corresponding to and equal in number to the number of individual wires contained in the data cable 164. First coupling 422 includes a key structure 442 to properly orient the first coupling 422 to a mating and complementary coupling arrangement disposed on the housing 104. Such key structure 442 may be provided on either one, or both, of the first coupling 422 and the mating and complementary coupling arrangement disposed on the housing 104. First coupling 422 may include a quick-connect type connector, which may be configured, for example, so that a simple pushing motion engages the first coupling 422 to the housing 104. Seals may be provided in conjunction with any of the several connectors to provide a fluid-tight seal between the interior of first coupling 422 and the environment.

Figure 1G:
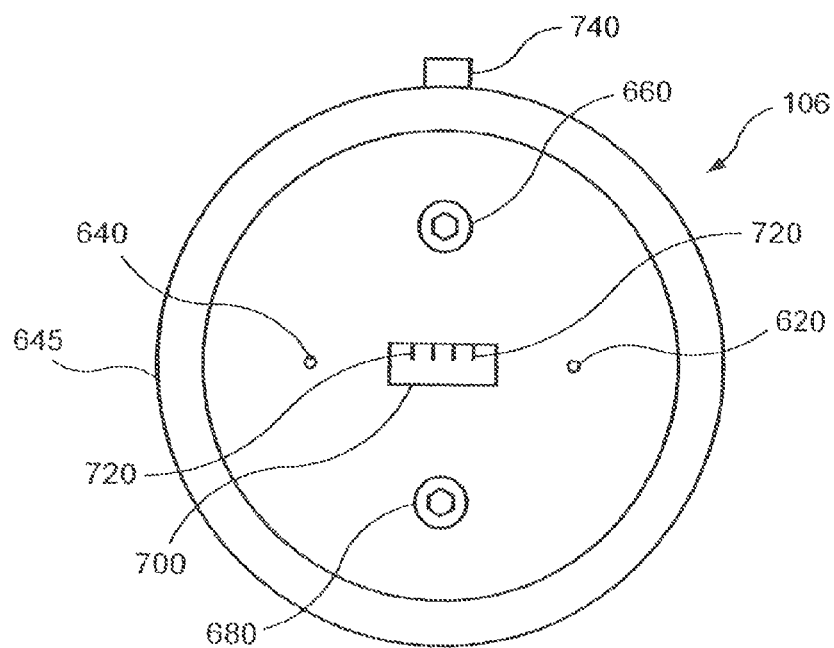
FIG. 1g is a front end view of a second coupling

FIG. 1*g* is a front end view of the second coupling 106 of flexible shaft 105. Second coupling 106 includes a first connector 660 and a second connector 680, each rotatably secured to the second coupling 106 and each non-rotatably secured to a distal end of a respective one of the first and second drive shafts 152, 154. A quick-connect type fitting 645 is provided on the second coupling 106 to detachably secure a surgical instrument or attachment thereto. The quick-connect type fitting 645 may include, for example, a rotary quick-connect type fitting, a bayonet type fitting, etc. A key structure 740 is provided on the second coupling 106 to properly align the surgical instrument or attachment to the second coupling 106. The key structure or other arrangement to properly align the surgical instrument or attachment to the flexible shaft 105 may be provided on either one, or both, of the second coupling 106 and the surgical instrument or attachment. In addition, the quick-connect type fitting may be provided on the surgical instrument or attachment. A data connector 700, having electrical contacts 720, is also provided in the second coupling 106. Like the data connector 60 of first coupling 422, the data connector 700 of second coupling 106 includes contacts 720 electrically and logically connected to the respective wires of data transfer cable 164 and contacts 462 of data connector 460. Seals may be provided in conjunction with the connectors 660, 680, 700 to provide a fluid-tight seal between the interior of second coupling 106 and the environment. In a further example embodiment, electrical contacts 620, 640 receive any additional voltage that may be sent from the remote power console 102 to the surgical instrument or device. In a further example embodiment, the surgical instrument or device may use the additional voltage provided by electrical contacts 620, 640 to charge electrodes that may be included within the surgical instrument or device.

Figure 1H:
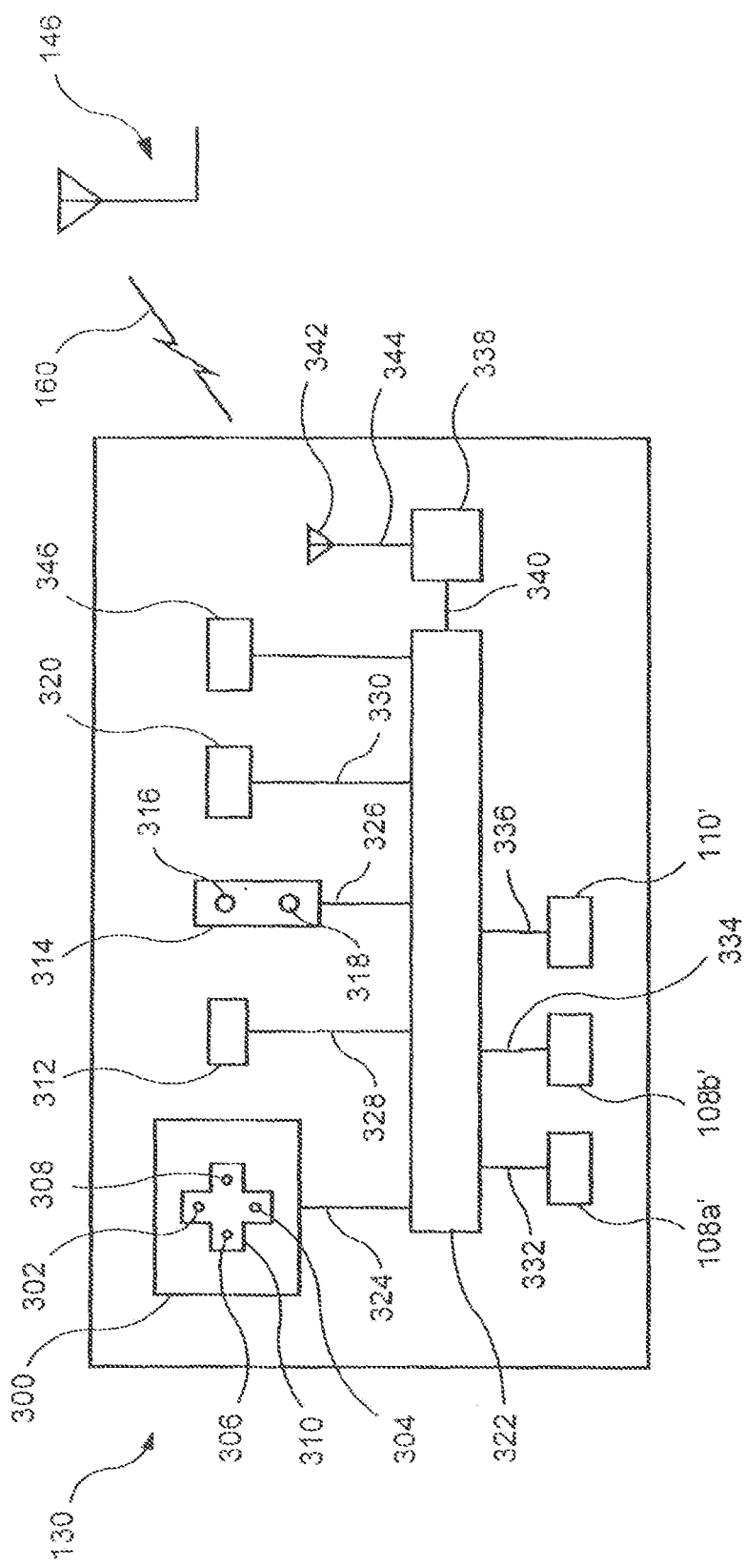
FIG. 1h is a schematic top view of another example embodiment of a remote control unit.

FIG. 1*h* illustrates an example embodiment of a wireless RCU 130 which provides the user with controls for the electro-mechanical device 101 and the surgical device 200. Wireless RCU 130 includes a steering engage/disengage switch 312, the operation of which controls the operation of one or more motors in order to selectively engage and disengage the steering mechanism. Wireless RCU 130 also may include a two-way rocker 314 having first and second switches 316, 318 operable thereby. The operation of these switches 316, 318 controls certain functions of the electro-mechanical surgical device 101 and any surgical instrument or attachment attached to the flexible shaft 105 in accordance with the operating program or algorithm corresponding to the attached surgical instrument or attachment, if any. For example, operation of the two-way rocker 314 may control the advancement and retraction of the flexible shaft 105. Wireless RCU 130 is provided with yet another switch 320, the operation of which may further control the operation of the electro-mechanical surgical device 101 and any surgical instrument or attachment attached to the flexible shaft 20 in accordance with the operating program or algorithm corresponding to the attached surgical instrument or attachment, if any. For example, when the surgical device 200 is attached to the flexible shaft 105, operation of the switch 320 may initiate the advancement of staples into tissue between jaws 4*a*, 4*b*.

Wireless RCU 130 may also include a controller 322, which is electrically and logically connected with the switches 302, 304, 306, 308 via line 324, with the switches 316, 318 via line 326, with switch 312 via line 328 and with switch 320 via line 330. Wireless RCU 130 may include indicators 108*a*', 108*b*', corresponding to the indicators 108*a*, 108*b* of front panel 103, and a display device 110', corresponding to the display device 110 of the front panel 103. If provided, the indicators 108*a*', 108*b*' are electrically and logically connected to controller 322 via respective lines 332, 334, and the display device 110' is electrically and logically connected to controller 322 via line 336. Controller 322 is electrically and logically connected to a transceiver 338 via line 340, and transceiver 338 is electrically and logically connected to a receiver/transmitter 342 via line 344. A power supply, for example, a battery, may be provided in wireless RCU 130 to power the same. Thus, the wireless RCU 130 may be used to control the operation of the electro-mechanical surgical device 101 and any surgical instrument or attachment attached to the flexible shaft 105 via wireless link 160.

Wireless RCU 130 may include a switch 346 connected to controller 322 via line 348. Operation of switch 346 transmits a data signal to the transmitter/receiver 146 of the remote power console 102, for example as illustrated in FIG.

1a, via wireless link 160. The data signal may include, for example, identification data uniquely identifying the wireless RCU 130. This identification data may be used by a controller within the electro-mechanical surgical or driver device 101 to prevent unauthorized operation of the electro-mechanical driver device 101 and to prevent interference with the operation of the electro-mechanical driver device 101 by another wireless RCU. Each subsequent communication between the wireless RCU 130 and the electro-mechanical driver device 101 may include the identification data. Thus, the controller may discriminate between wireless RCUs and thereby allow only a single, identifiable wireless RCU 130 to control the operation of the electro-mechanical driver device 101 and any surgical instrument or attachment attached to the flexible shaft 105. In another example embodiment, RCU 130 is connected to remote power console 102, for example, as illustrated in FIG. 1a, via wires or an optical connection.

FIGS. 2a to 2e illustrates further example embodiments of a surgical device 200' having expandable jaws that remain parallel. In such example embodiments, surgical device 200' includes a parallel separable jaw system that has a lower jaw 40b and an upper jaw 40a having a proximal end 220.

Figure 2A:
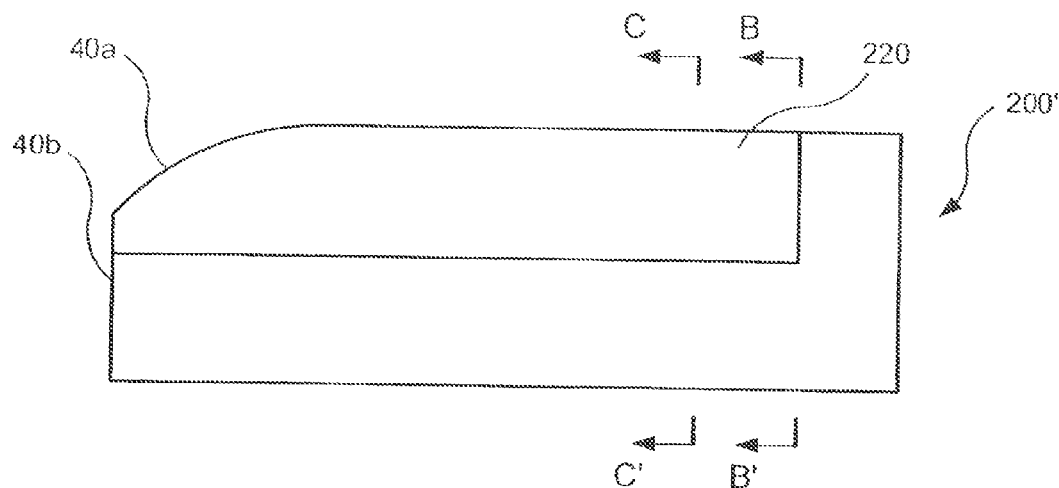
FIG. 2a illustrates an example embodiment of parallel expanding jaws in a closed position.
Figure 2B:
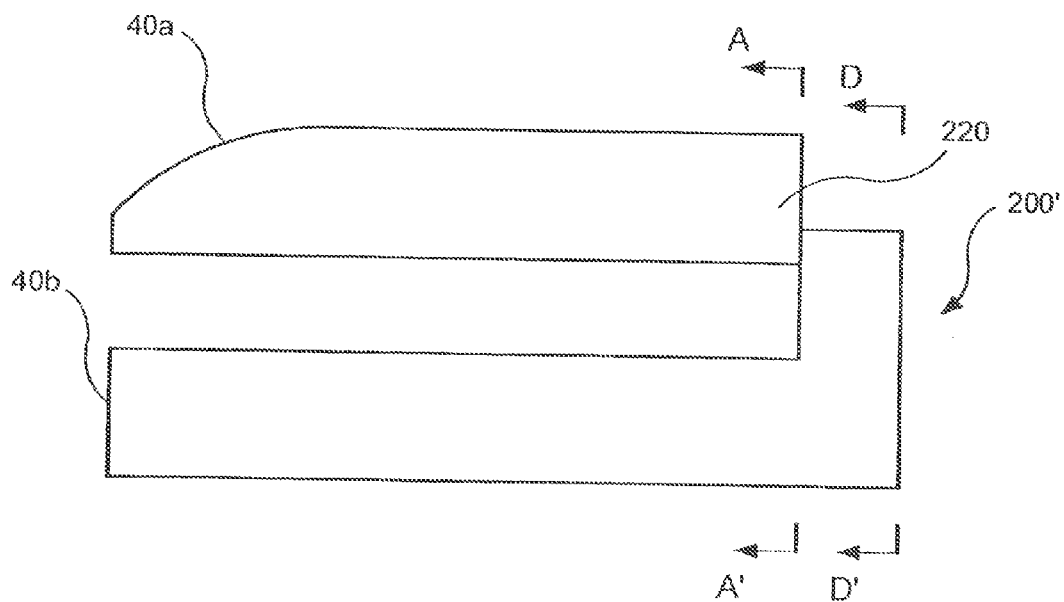
FIG. 2b illustrates an example embodiment of parallel expanding jaws in an open position.
Figure 2C:
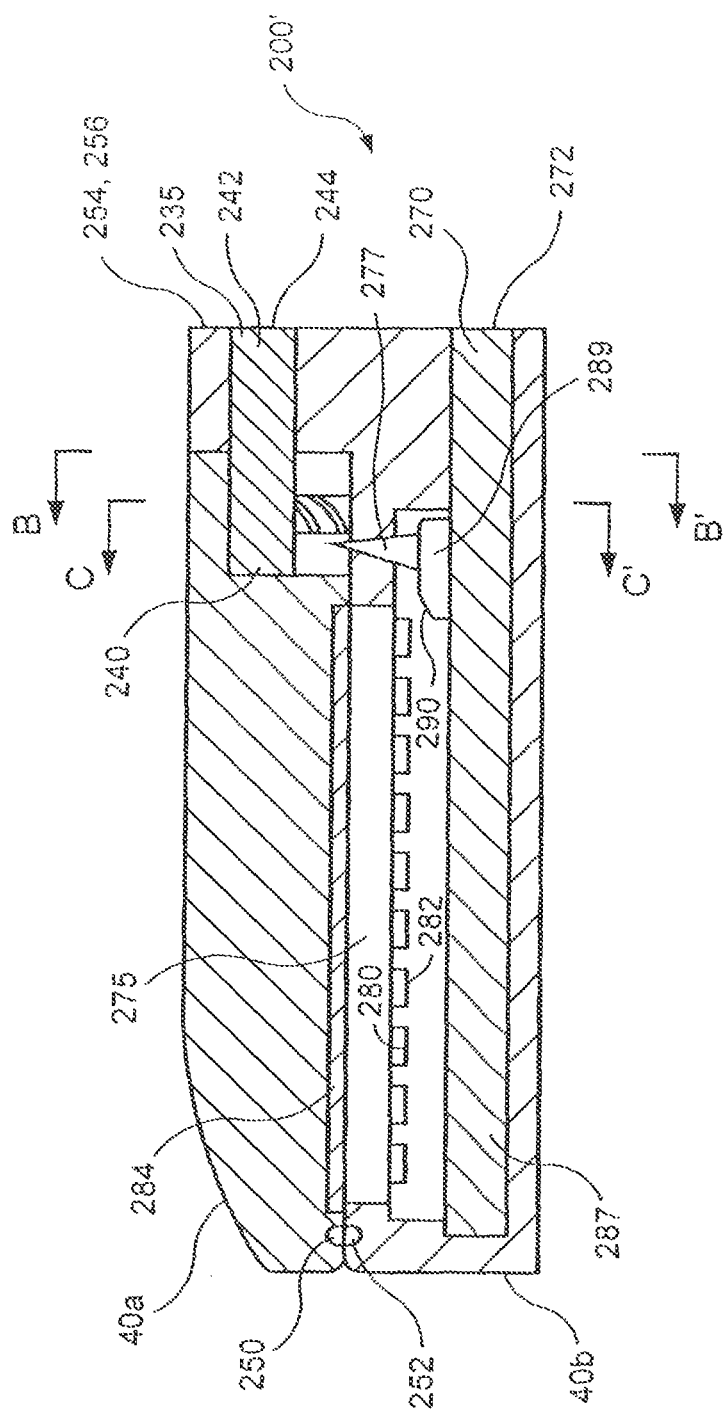
FIG. 2c illustrates an example embodiment of the components of the parallel expanding jaws in a closed position.
Figure 2D:
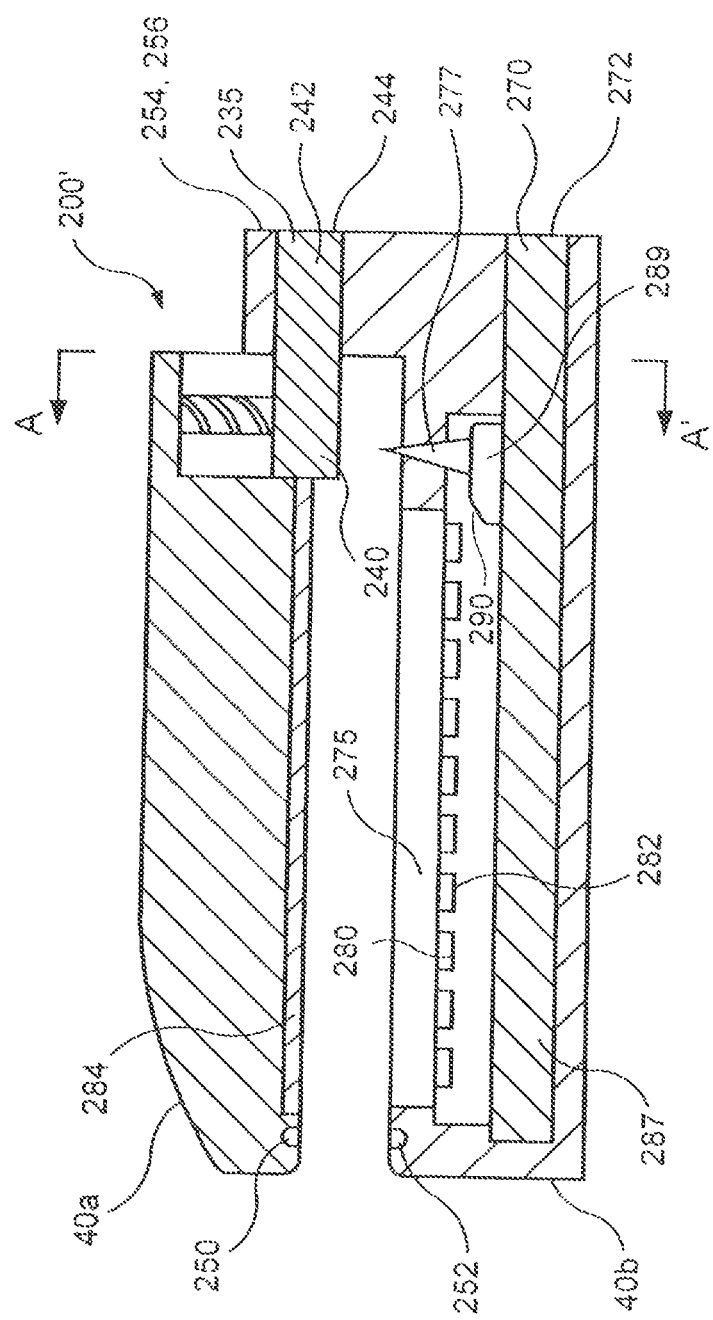
FIG. 2d illustrates an example embodiment of the components of the parallel expanding jaws in an open position.
Figure 2E:
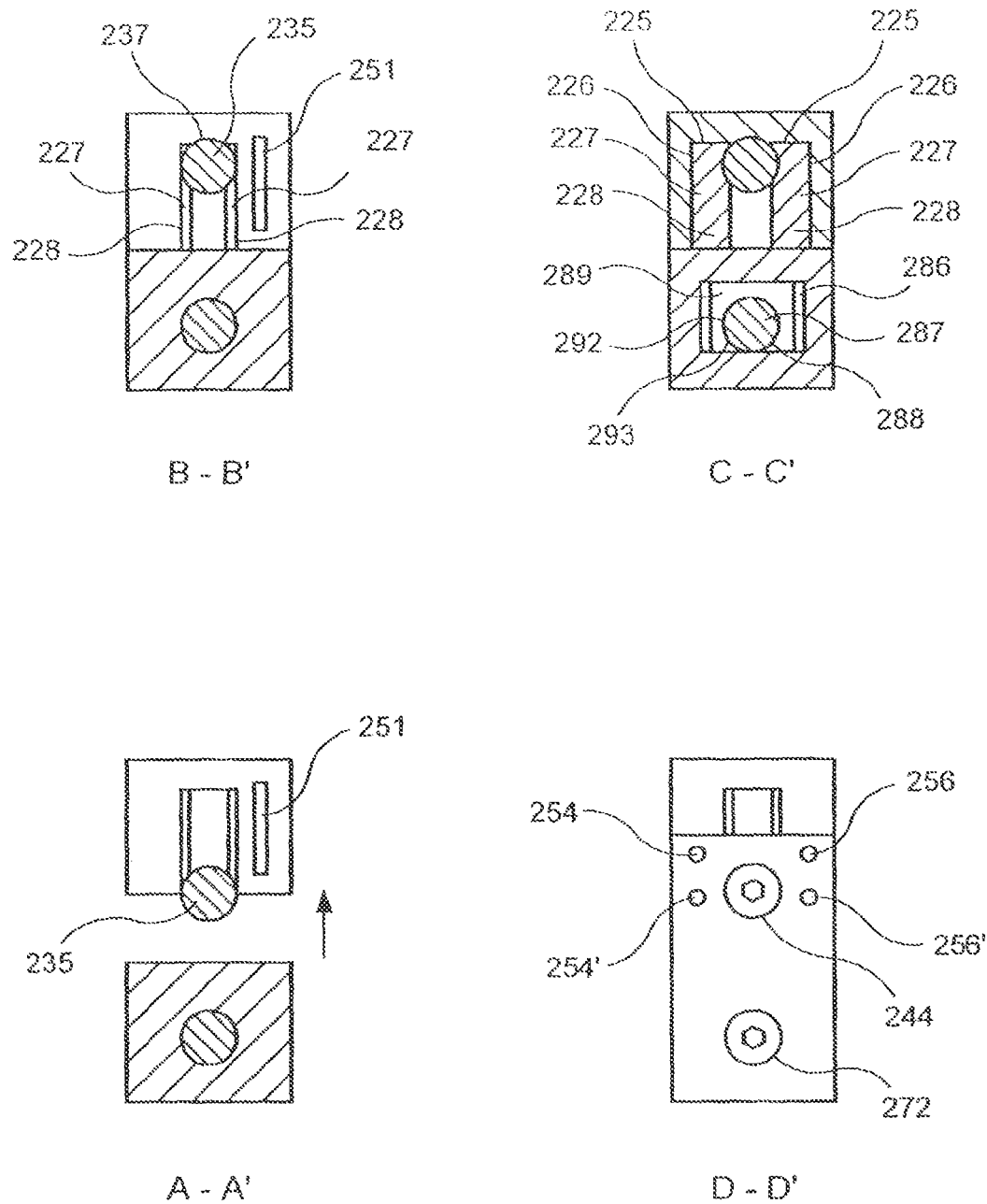
FIG. 2e is cross-sectioned view of the parallel expanding jaws.

Referring to FIGS. 2c, 2d and 2e, the proximal end 220 of the upper jaw 40a has a pair of threaded vertical bores 225, through which extend a corresponding pair of vertical shafts 227. Inner threads 226 of the vertical bores 225 match outer threads 228 of the vertical shafts 227. The vertical shafts 227 engage a threaded upper horizontal shaft 235 at a distal end 240 of the upper horizontal shaft 235. Outer threads 237 of the upper horizontal shaft 235 interlock with the outer threads 228 of the vertical shafts 227. The upper horizontal shaft 235 has at a proximal end 242, an upper drive socket 244.

The example embodiments of the surgical device 200' as illustrated in FIGS. 2a to 2e attaches to coupling 106 of the electro-mechanical driver device 101 such that an upper drive socket 244 and a lower drive socket 272, illustrated in FIG. 2e, engages the flexible shaft 105 at the distal end 109. Thus, rotation of the upper horizontal shaft 235 is effected by rotation of the upper drive socket 244 which is effected by rotation of the corresponding flexible drive shaft of flexible shaft 105. Clockwise or counter-clockwise rotation is achieved depending on the direction of the corresponding motor within the remote power console 102. Similarly, rotation of the lower horizontal shaft 287 is effected by rotation of the lower drive socket 272 which is effected by rotation of the corresponding flexible drive shaft of flexible shaft 105. Also, the clockwise or counter-clockwise rotation of the lower horizontal shaft 287 is achieved depending on the direction of the corresponding motor within remote power console 102. Surgical device 200' also includes contact nodes 254', 256' which transfer additional voltage to surgical device 200'.

As illustrated in FIGS. 2c and 2d, the surgical device 200' further includes a first sensor electrode 250 configured to electrically communicate via communication wires with a first contact pad 251, which is configured to electrically communicate with a second contact pad via direct contact, which is configured to electrically communicate via communications wires with a first contact node 254, as illustrated in FIGS. 2c and 2d. Similarly, the surgical device 200' further includes a second sensor electrode 252 configured to electrically communicate via communication wires with a second contact node 256. The contact nodes 254, 256 are configured to electrically communicate with communication wires in the electro-mechanical driver device 101 to form a sensor circuit, such that when the upper jaw 40a and the lower jaw 40b are clamped together, the sensor electrodes 250, 252 are in contact, the sensor circuit is closed, and the surgeon is alerted via other circuit components to the clamped position of the jaws 40a, 40b, and is therefore informed that it is safe and/or appropriate to active the stapling mechanism.

The example embodiment illustrated may include a wedge pushing system within lower jaw 40b. FIGS. 2c and 2d show the wedge pushing system including a replaceable tray or cartridge 275 housing one or more fastening staples, and an upper jaw 40a one or more staple guides 284 corresponding to the staples 280. Each of the staples 280 has a butt 282 protruding below the tray 275 and a pair of prongs 284 extending to the top of the tray 275. The wedge pushing system further includes a wedge guide, or channel 286, illustrated in FIG. 2e, extending beneath the tray 275. Within the channel 286 extends a threaded lower horizontal shaft 287 having outer threads 288. Upon the lower horizontal shaft 287 is arranged a wedge 289 having a sloped top face 290, a horizontal threaded bore 292 coaxial with the channel 286, having inner threads 293 matching the outer threads 288 of the lower horizontal threaded shaft 287, and an upwardly extending cutting member 277.

Figure 2F:
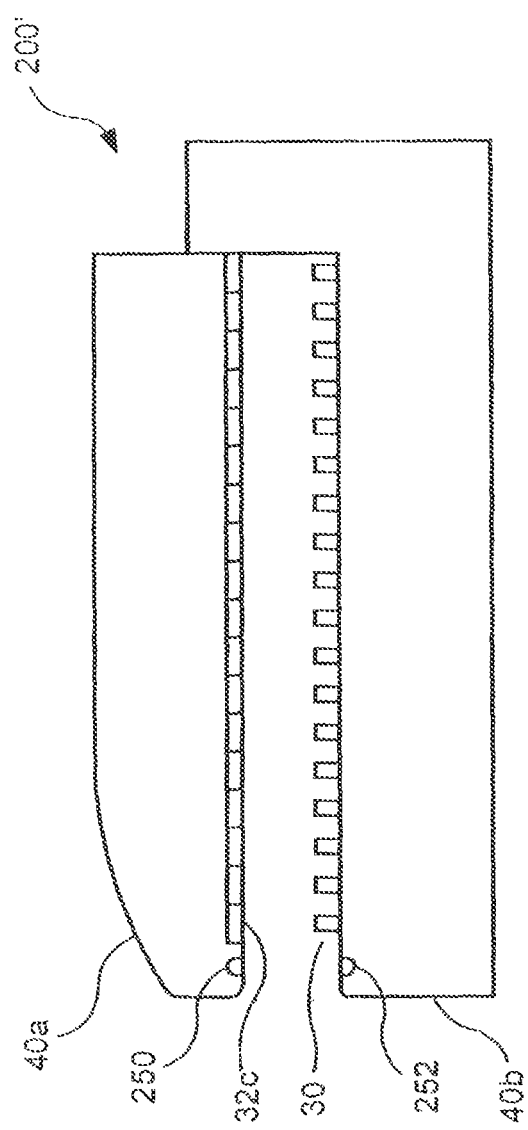
FIG. 2f illustrates an example embodiment of the parallel expanding jaws where the lower jaw includes electrodes.

FIGS. 2f to 2k illustrate various electrode and/or stapling mechanism configurations associated with the surgical device 200' illustrated in FIGS. 2a to 2e. FIG. 2f is a side view of the jaws 40a, 40b. As illustrated in FIG. 2f, the surgical device 200' includes electrodes 30 disposed over lower jaw 40b, a pierceable ampullae 32c, which may be similar to pierceable ampullae 5 described above, and sensors 250, 252. Electrodes 30 protrude from the lower jaw 40b and are applied to and may pierce tissue placed between the jaws in order to anastomose the tissue. Accordingly, the electrodes 30 may be rigid and conductive in regard to the material used for their construction. The electrodes 30 may also have features that may enhance tissue penetrating attributes and electrical contact between any opposing electrodes. Various configurations may be provided to enhance contact with tissue where electrode height, width and density of spacing are adjusted in order to accommodate various tissue thickness and texture. The electrodes 30 are charged through voltage sent from remote power console 102 through leads 166, 168 of flexible shaft 105. Contact nodes 254', 256' electrically connect to electrical contacts 620, 640 of coupling 106 and current flows through to electrodes 30. As described above, electrical contacts 620, 640 are electrically connected to leads 166, 168 of the flexible shaft 105. Sensors 250, 252 monitor the amount of heat generated by the charging of electrodes 30 and duration of application. Sensors 250, 252 transfer signals to the remote power console 102 which provides the user with information regarding current conditions related to the operation of the surgical device 200'.

Figure 2G:
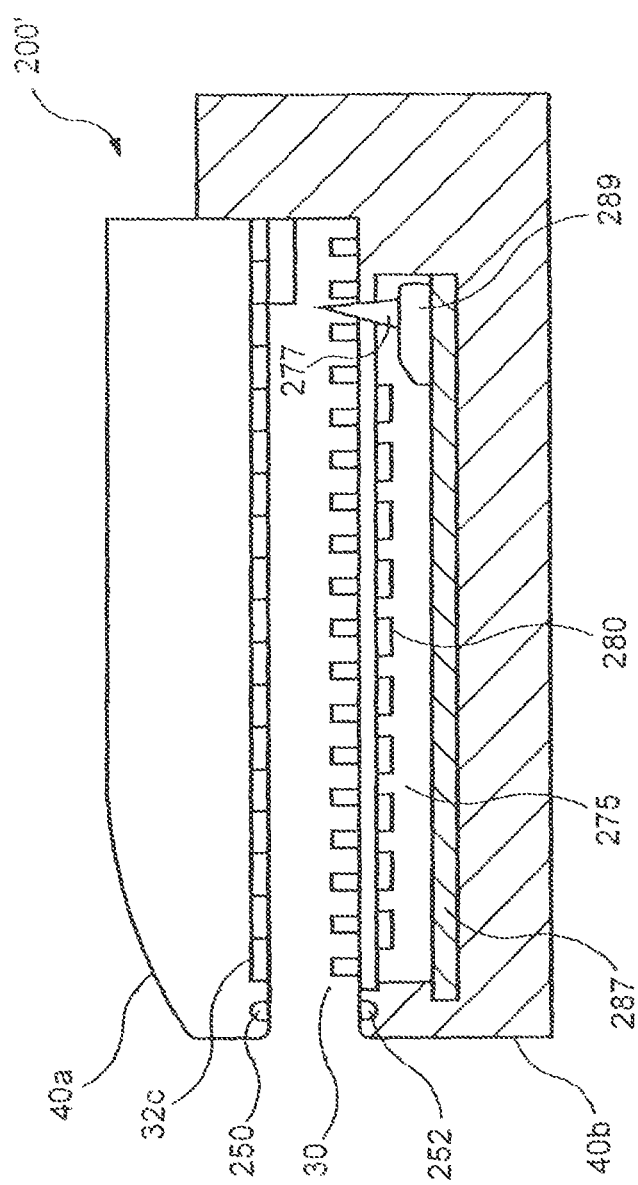
FIG. 2g illustrates an example embodiment of the parallel expanding jaws where the lower jaw includes electrodes and a stapling mechanism.

FIG. 2g illustrates the electrodes 30 used in conjunction the wedge pushing system as described above. In this example embodiment, the wedge pushing system is similar the wedge pushing system as described with reference to FIGS. 2e to 2d. The wedge pushing system is operated in conjunction with the electrodes 30 in order to coagulate and/or anastomose tissue between the parallel jaws 40a, 40b.

Figure 2H:
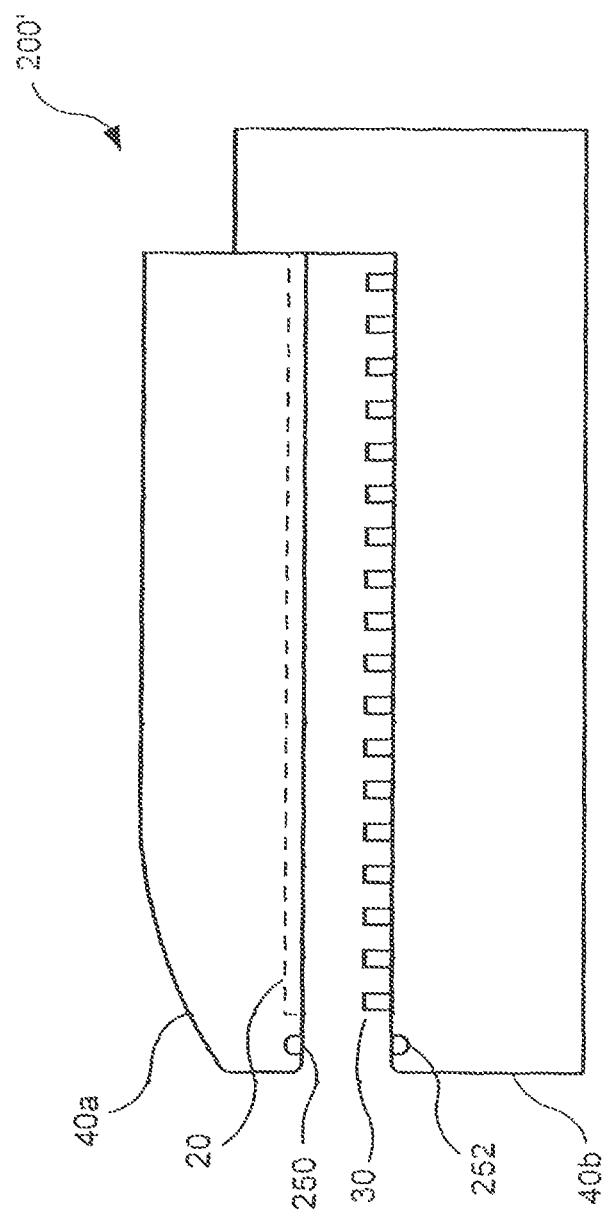
FIG. 2h illustrates another example embodiment of the parallel expanding jaws where the lower jaw includes electrodes.
Figure 2I:
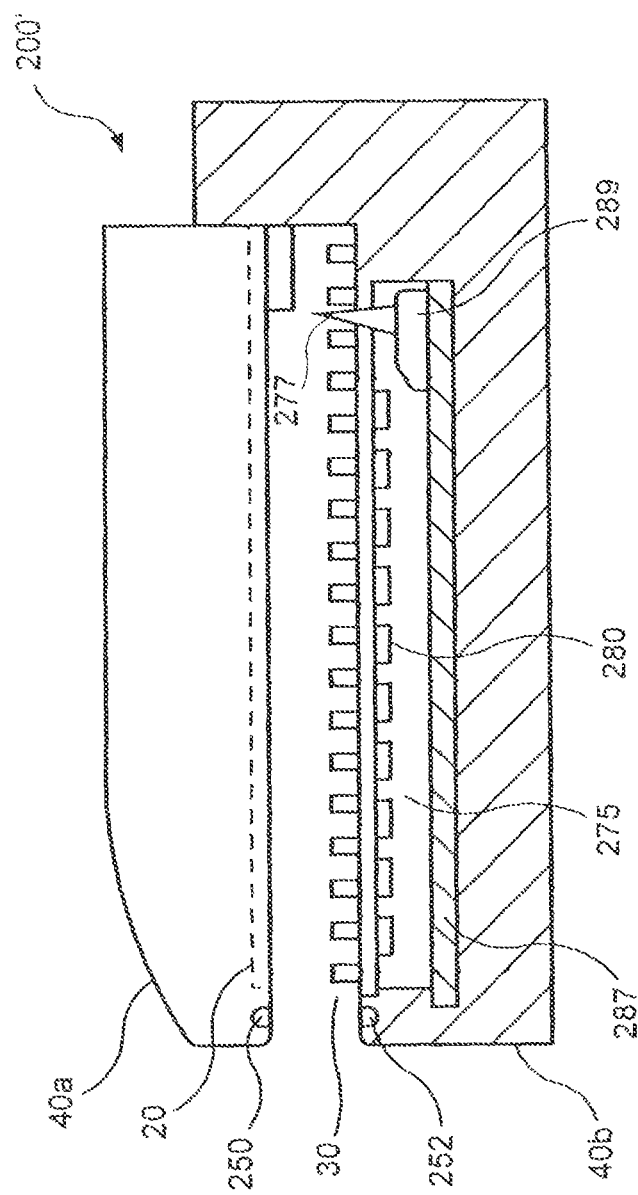
FIG. 2i illustrates another example embodiment of the parallel expanding jaws where the lower jaw includes electrodes and a stapling mechanism.

FIG. 2h illustrates an electrode configuration of another example embodiment of the present invention. As illustrated electrodes 30 are disposed over the inner face of the lower jaw 40b. The electrodes 30 are charged positively and receptacles 20 are negatively charged (ground) and configured for alignment with electrodes 30. This configuration induces current to flow from lower jaw 40*b* to the upper jaw 40*a* when the jaws 40*a*, 40*b* are closed. The amount of RF energy transferred between jaws 40*a*, 40*b* may be varied depending upon whether staples are used in conjunction with the electrodes, as illustrated in FIG. 2*i*, or if the anastomose is performed solely through the use of the electrode configuration. In an example embodiment, the electrodes 30 and receptacles 20 electrically communicate with the remote power console 102 through contact nodes 254', 256' as described above in reference to FIGS. 2*f* and 2*g*. As described above with reference to FIG. 2*g*, FIG. 2*i* illustrates the electrode configuration illustrated in FIG. 2*h* used in conjunction with the wedge pushing system which provides a stapling mechanism.

Figure 2J:
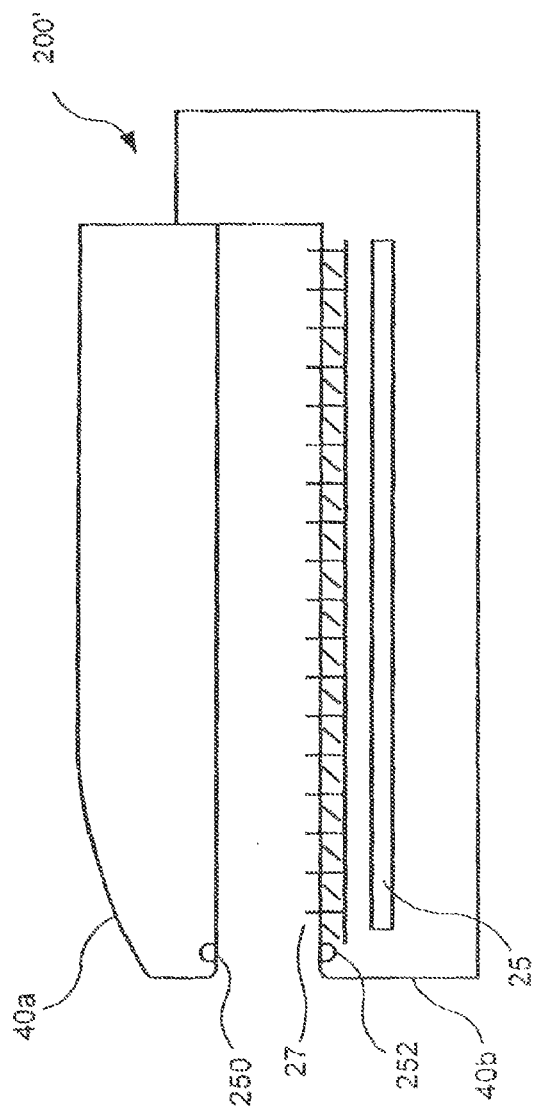
FIG. 2j illustrates an example embodiment of the parallel expanding jaws which includes ultrasonic pins.

FIG. 2*j* illustrates yet another example embodiment of the present invention is illustrated. The electrode configuration illustrated in FIG. 2*j* provides ultrasonic energy which is transmitted through ultrasonic resonator pins 27 which are configured on the inner surface of the lower jaw 4*b*. Similar to the electrode configurations described above, the ultrasonic pins 27 may be configured in various formations conducive to the type and form of the tissue which is placed between the jaws for coagulation, anastomosing and/or cutting. In addition to the ultrasonic resonator pins 27, the lower jaw 4*b* also includes an ultrasonic transducer 25. The ultrasonic transducer 25 generates the ultrasonic energy that resonates through the pins 27. The ultrasonic resonator pins 27 may be used with or without staples, as described with regard to the electrode configurations above, enable the reduction of the number of staples used or the elimination thereof and lessen the mechanical force needed in order to complete coagulation and cutting. The ultrasonic energy use in this example embodiment may be transmitted through contact nodes 254', 256' as described in the foregoing example embodiments.

Figure 2K:
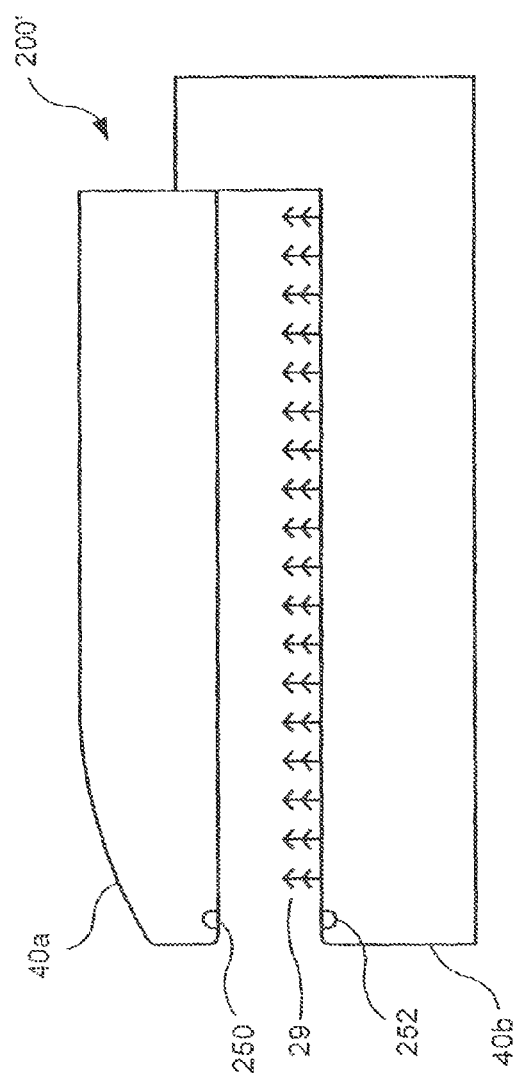
FIG. 2k illustrates an example embodiment of the parallel expanding jaws which includes surgical barb pins.

FIG. 2*k* illustrates yet another example embodiment of the present invention in which electrodes 29 are configured as surgical barbs. The configuration of electrodes 29 provide for an improved configuration for penetrating tissue. The electrodes 29 may follow the polarity schemes described above in order apply RF energy to the tissue. The electrodes 29 may be used as illustrated with electrodes arranged on the lower jaw 40*b* only. However this surgical barb type electrode may also be arranged on the inner surface of the upper jaw 40*a* in order to provide even more effective penetrating results. Furthermore, as described above with reference to FIG. 2*f*, a pierceable ampulla 32*c* may be incorporated in the upper jaw 40*a* and used to induce hemostasis. The electrodes 29 receive the RF energy through contact nodes 254', 256' as described in the foregoing example embodiments.

Figure 3A:
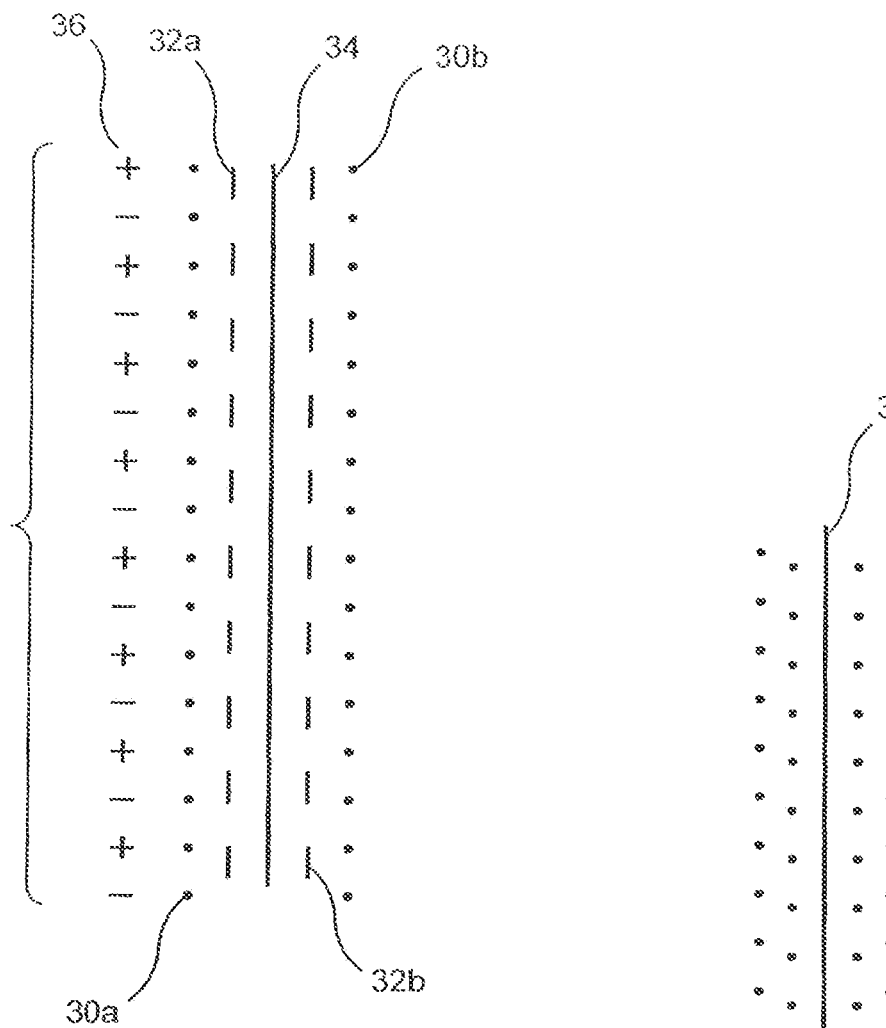
FIG. 3a illustrates an example embodiment of an electrode and staple configuration according to the present invention.

FIG. 3*a* is a view of an example electrode/staple configuration which may be disposed on the inner surface of lower jaw 4*a* or lower jaw 40*a*. As illustrated, in this example embodiment, this configuration includes two rows of electrodes 30*a*, 30*b*, two rows of staples 32*a*, 32*b* and a cutting device 34. The cutting device 34 is between the rows of staples 32*a*, 32*b*, and electrodes 30*a*, 30*b* is outside of the rows of staples 32*a*, 32*b*. The polarities 36 associated with the respective electrodes are indicated to the left of electrodes 30*a*. In this example embodiment, the polarities 36 of the electrodes alternate between positive ("+") and negative ("−") along the vertical row of electrodes. In operation, the RF energy applied to the electrodes corresponds the polarities as indicated. The alternating polarities allow for current to pass from one electrode to another where the current travels parallel to the electrode members 30*a*, 30*b*. In an alternative example embodiment, each row of electrodes may be either all positive or all negative. In this example embodiment, corresponding contacts of opposite polarity may be provided on the upper jaw 4*b*.

Figure 3D:
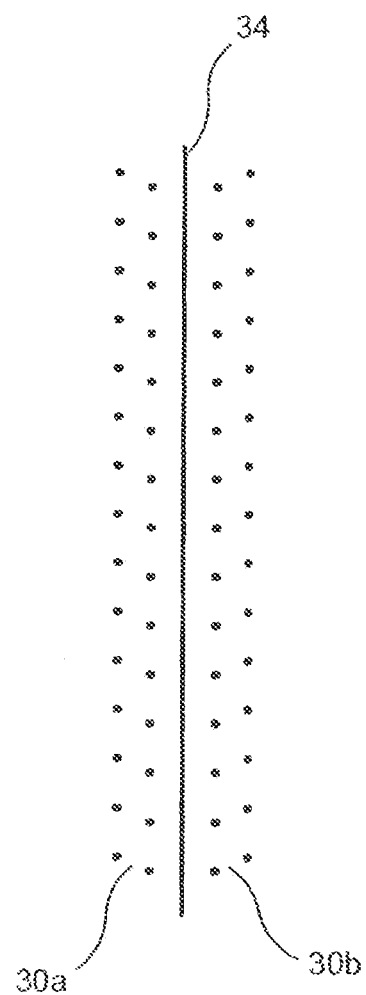
FIG. 3d illustrates an example embodiment of an electrode configuration according to the present invention.
Figure 3B:
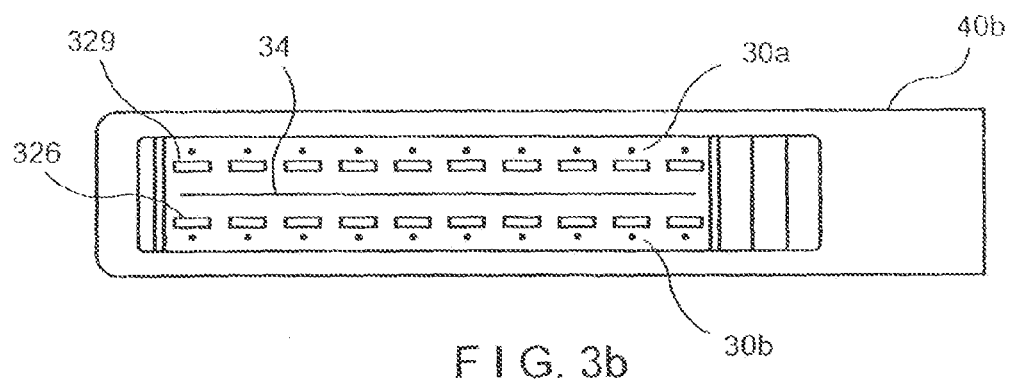
FIG. 3b illustrates an example embodiment of an electrode and staple configuration disposed on a lower jaw.

FIG. 3*b* illustrates the electrode and staple configuration of FIG. 3*a* on the lower jaw 40*b*. The example embodiment illustrated in FIG. 3*b* includes the rows of electrodes 30*a* and 30*b* which during operation receive their charge via current supplied through leads 166, 168 of flexible shaft 105 from the remote power console 102, as described above. The polarities associated with the rows of electrodes 30*a*, 30*b* may vary as described above and illustrated in FIG. 3*a*. In one example embodiment, the user controls the movement of flexible shaft 105, the actuation of jaws, the movement of staples and the polarities and charge associated with the electrodes by using RCU 130 in conjunction with remote power console 102.

The configuration illustrated in FIG. 3*a* may be placed on the inner surface of the lower jaw 4*b*, 40*b* or disposed on both jaws of surgical device 200. The electrodes 30*a*, 30*b* provided may be bipolar and may be arranged in various configurations which create either alternating or opposing polarities as explained below in the various example embodiments described. In operation, the present invention may be used with one row of staples or no staples to enable the closure of tissue.

If the configuration illustrated in FIG. 3*a* is used on the inner surfaces of both jaws 4*a*, 4*b*, the polarities of electrodes may be the same for both jaws 4*a*, 4*b* which may allow current to flow parallel to the respective columns of electrodes. Alternatively, the polarities of the electrodes may be switch between the jaws 4*a*, 4*b*, where opposite polarities may exist for the respective corresponding electrode columns between the jaws 4*a*, 4*b* which may allow current to flow between jaws 4*a*, 4*b* once they are in a closed position.

Figure 3C:
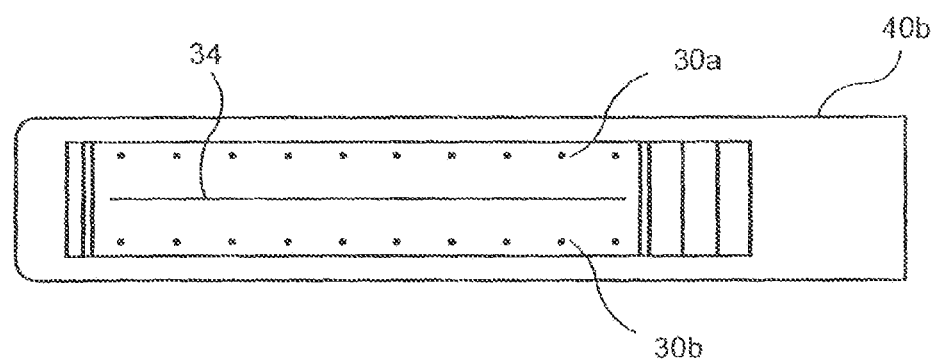
FIG. 3c illustrates an example embodiment of an electrode configuration disposed on a lower jaw.
Figure 3E:
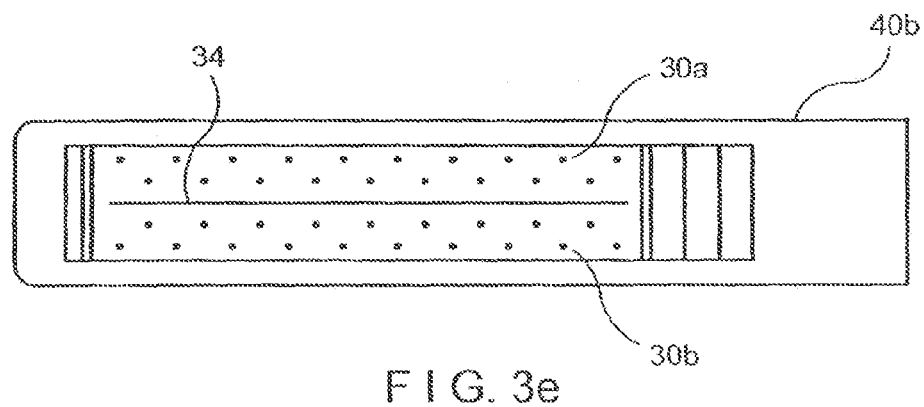
FIG. 3e illustrates an example embodiment of an electrode configuration disposed on a lower jaw.

Another example embodiment is illustrated in FIG. 3*c*, in which two rows of electrodes 30*a* and 30*b* are illustrated without any staples or stapling configuration. The example embodiment illustrated in FIG. 3*c* solely involves the use of electrodes which may induce an appropriate level of heat in order to coagulate tissue during operation. FIG. 3*d* illustrates an alternative electrode configuration. The electrodes are arranged with two electrode rows on each side of cutting device 34. FIG. 3*e* illustrates the dual row of electrode configuration 30*a*, 30*b* on the inner surface of lower jaw 40*b*.

In another example embodiment of the present invention, staple lines may be removed from the electrode configuration as illustrated in FIGS. 3*c* and 3*d*. FIG. 3*d* illustrates four rows of electrodes 30*a*, 30*b* where two columns are placed on each side of the cutting device 34. The electrodes may have alternating polarities of RF energy applied in order to produce a current flow. Polarities may alternate vertically, or an entire column of electrodes may be positively charged and the respective adjacent column may be negatively charged in order to induce current flow between the two columns on each respective side of cutting device 34. As described with the electrode configuration illustrated in FIG. 3*a*, the electrode configurations illustrated in FIGS. 3*c* and 3*d* may be placed on both inner surfaces of jaws 4*a*, 4*b*. Also, the upper jaw 4*a* may incorporate pierceable ampulla and function, as described above, with electrodes 30 as illustrated in FIG. 2*f*. In the example embodiments, described above, electrodes configured to pierce tissue are illustrated. Of course, it is also possible to use surface-type electrodes to perform coagulation and/or anastomosing.

Figure 4A:
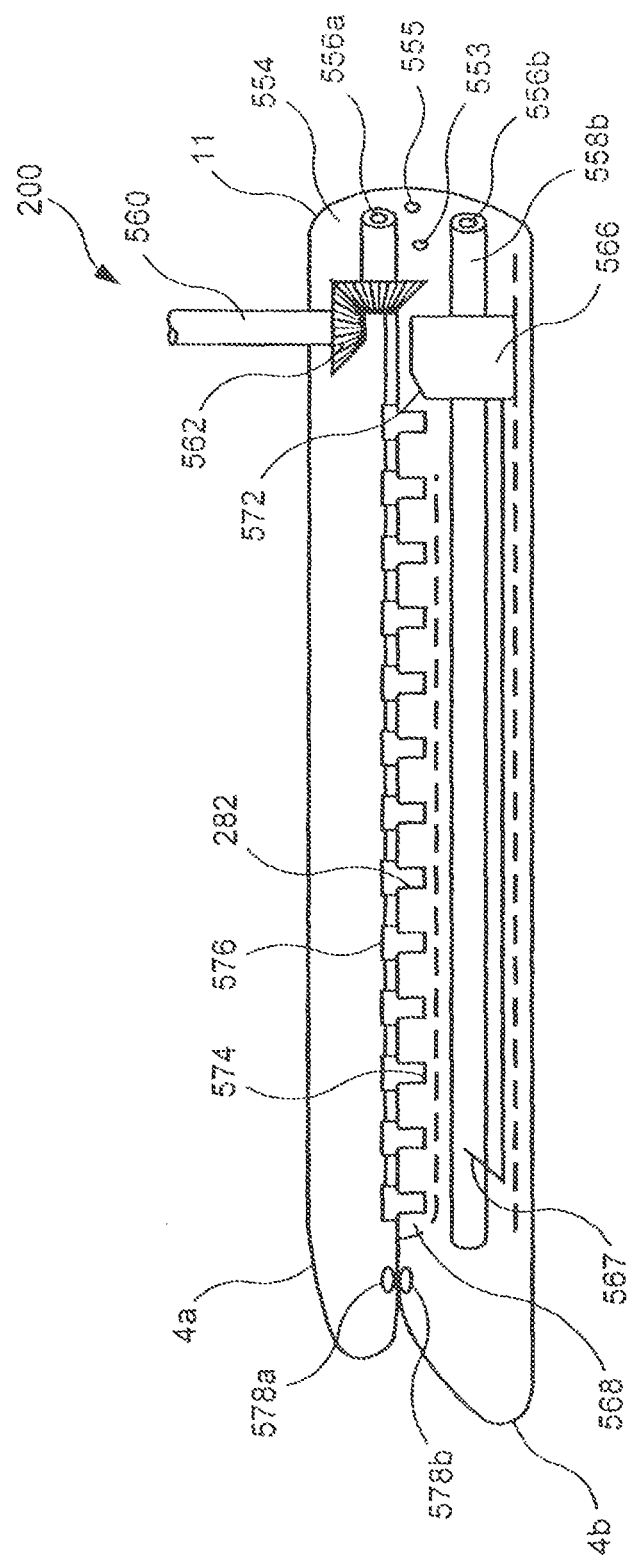
FIG. 4a illustrates an example embodiment of scissor-like jaws in a closed position.
Figure 4B:
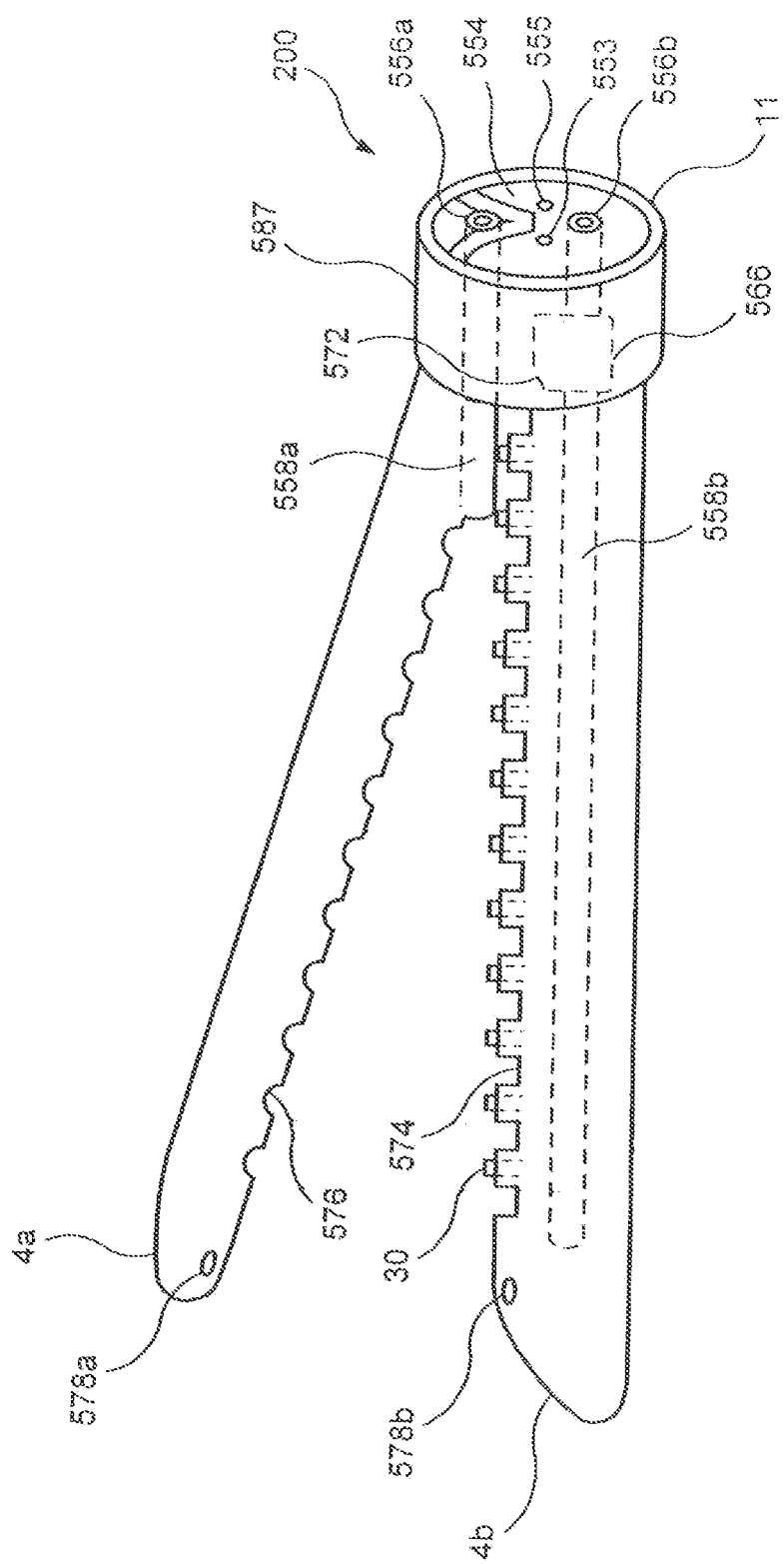
FIG. 4b illustrates an example embodiment of scissor-like jaws in an open position.

FIGS. 4*a* and 4*b* illustrate two alternative example embodiments of surgical device 200 according to the present invention. The first example embodiment, illustrated in FIG. 4a, includes a separating jaw system including a lower jaw 4b, an upper jaw 4a and a coupling 11. Coupling 11 includes two hexagonal shaped sockets 556a, 556b into which coupling 106 of flexible shaft 105 fits. Each of the sockets is formed in the end of a corresponding horizontal turning shaft 558a, 558b. The upper horizontal turning shaft 558a is coupled, by a transverse gearing member, to a threaded vertical shaft 560 which extends through a correspondingly threaded bore 562 of the upper jaw 4a. The upper jaw 4a has a linear track coupling means 566 which corresponds and couples to a linear track 568 formed in the side of the interface end member 554 which is opposite the driver coupling sockets 556a, 556b. Subsequent turning of the upper horizontal turning shaft 558a causes the vertical turning shaft 560 to turn. As this shaft 560 turns, the upper jaw 4a rides up and down within the track of the end member 554.

The lower horizontal turning shaft 558b extends axially through the lower jaw 4b, which, in turn is fixed to the proximal end member 554. Mounted around this axially extending shaft 558b is a wedge driver mechanism 566 which includes a threaded bore. This threaded member 566 is locked within a track 567, which prevents the member 566 from rotating when the shaft 558b turns. Rather, the wedge member 566 rides linearly along the track 567 and along the threading of the shaft 558b. Mounted within a recess 568 in the face of the lower jaw 4b which opposes the upper jaw 4a directly above the wedge member 566 is a replaceable tray of staples. The wedge driver has a sloped frontal surface 572 which contacts the staples 282 and causes it to be driven upwardly. When the upper jaw 4a is in close proximity to the lower jaw 4b, the staples are closed when they contact the opposing face of the upper jaw 4a by the action of staple closing guide recesses 576 formed therein.

At the distal tip of the upper and lower jaws are two opposing magnetic sensors 578a, 578b, each coupled to a circuit component which connects to the electro-mechanical driver 102 via flexible shaft 105. When the jaws come together, the circuit is closed, and indicators 108a and 108b provide a signal indicating that the staples may be safely fired.

Referring now FIG. 4b, another example embodiment of the surgical device 200 of the present invention is described. In the example embodiment, the coupling 11 is substantially equivalent to the first example embodiment. As before, the shafts of the driver component turn rotating members within the attachment. In this example embodiment however, both turning members 558a, 558b are horizontal. Mounted to the shaft interfacing member is a fixed lower jaw 4b and a moving upper jaw 4a. In this example embodiment, the upper jaw 4a is mounted to the lower jaw 4b by a spring loaded pivot, which biases the upper jaw 4a into an open disposition relative to the lower jaw 4b. Mounted to the upper turning shaft however, is a linearly tracked cuff 587 which seats around the upper and lower jaw, the advancement of which causes the jaws to come together. The lower jaw includes the same staple 574 tray recess and linearly driven threaded wedge staple pushing mechanism 566. Also, the electromagnetic sensor and circuit of the first example embodiment is included to indicate to the surgeon when the section of tissue has been fully clamped and the staples should be driven.

More particularly, after the surgeon has resected the diseased portion of the tissue, the end of the tissue is placed between the jaws of the attachment. By actuating a trigger and driving the upper shaft, the cuff member 587 advances axially along the outside of the upper and lower jaws 4a, 4b, thus closing the upper jaw onto the tissue and lower jaw. Once fully closed, the electromagnetic sensor circuit indicates to the surgeon operator that the staples may be fired, and correspondingly, actuation of the second trigger causes the wedge driver to advance and drive the staples through the tissue section. Reverse rotation of the motor for the upper turning shaft causes the cuff to retract and the upper jaw to open, thus releasing the now-sealed tissue end.

The surgical device 200 as illustrated in FIGS. 4a and 4b may also include electrodes used either in conjunction with the stapling mechanism or alone. FIG. 4b illustrates a row of electrodes 30 disposed along the lower jaw 4b. The electrodes 30 may receive RF energy through contacts 553, 555, similar to the energy transfer to the electrodes of the surgical device 200' as described above. Furthermore, the example embodiments illustrated in FIGS. 4a and 4b may include pierceable ampullae as described above with reference to FIGS. 1d and 2f. The surgical device 200 as illustrated in FIGS. 4a and 4b, may incorporate the various electrode and/or stapling configurations described above with reference to FIGS. 3a to 3e.

Figure 5A:
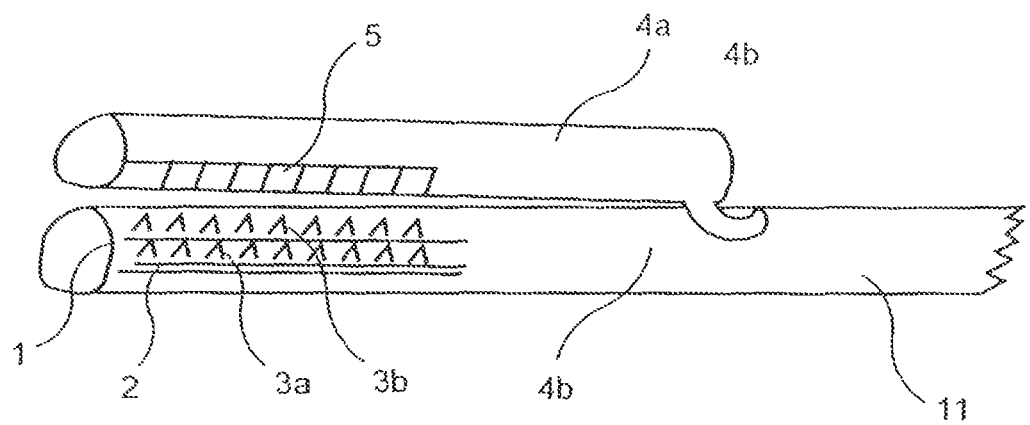
FIG. 5a illustrates a perspective view of an example embodiment of the present invention.

FIG. 5a is a perspective view of the present invention. Upper jaw 4a and lower jaw 4b are attached to a shaft 11 which connects to a electro-mechanical device 6. In operation, these jaws 4a, 4b are closed in order to coagulate and cut tissue positioned between them. As illustrated, the jaws 4a, 4b are attached to a first end of shaft 11 wherein the second end of shaft 11 connects to the electro-mechanical device 6. The electro-mechanical device 6 controls the movement of shaft 11 and jaws 4a, 4b. The shaft 11 may be flexible or rigid and may enable the mechanical actuation of the jaws 4a, 4b. The jaws 4a, 4b may include electrode members 3a, 3b on the inner surface of lower jaw 4b, or the electrode members 3a, 3b may be provided on both jaws 4a and 4b. The electrode members 3a, 3b provided on the lower jaw 4b may be bipolar and may be arranged in various configurations which create either alternating or opposing polarities. In operation, the present invention may be used with one row of staples or no staples to enable the closure of tissue. The jaws 4a, 4b mechanically and electrically accomplish the desired functions, i.e., cutting and coagulating tissue.

Figure 5B:
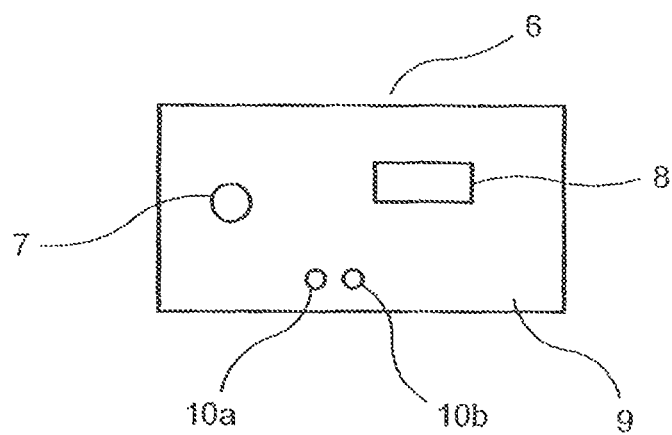
FIG. 5b illustrates an example embodiment of a front panel of an electro-mechanical device.

The second end of the shaft 11, illustrated in FIG. 5a, connects to electro-mechanical device 6, illustrated in FIG. 5b, at a shaft connection 7. The shaft 11 includes cables which transmit signals that control the movement of the DLU and the actuation of jaws 4a, 4b.

FIG. 5b illustrates other components of front panel 9, including a display device 8 and indicators 10a, 10b which provide positioning information to the user.

Figure 6:
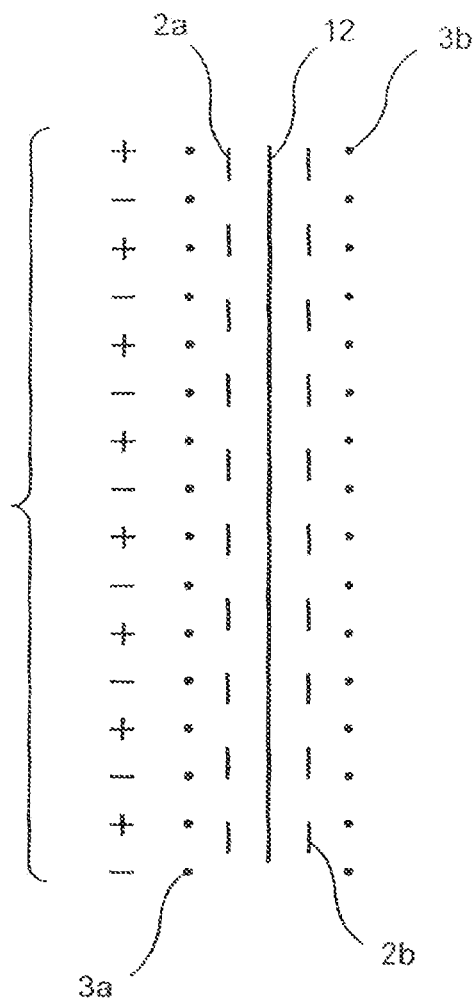
FIG. 6 illustrates an example embodiment of an electrode arrangement according to the present invention.

FIG. 6 illustrates an electrode configuration according to the present invention. This electrode configuration may be provided on the inner surface of lower jaw 4b or on both jaws 4a, 4b. The inner surface of lower jaw 4b includes two columns of electrode members 3a, 3b, two staple lines 2a, 2b and a cutting blade 12. The cutting blade 12 is between the staple lines 2a, 2b and electrode members 3a, 3b is outside of the staple lines 2a, 2b. The polarities associated with the respective electrodes are indicated to the left of electrode members 3a. The polarities of the electrodes alternate between + and − along the vertical column of electrodes. In operation, the RF energy applied to the electrodes corresponds the polarities as indicated. The alternating polarities allow for current to pass from one electrode to another where the current travels parallel to the electrode members 3a, 3b.

The upper jaw 4a may incorporate pierceable ampulla 5, shown in FIG. 5a, which may contain fluid for hemostasis. This fluid or matter, e.g., collagen, fibrin, dye, matter configured to effect anastomosis, matter configured to seal tissue and matter configured to effect hemostasis, etc., may be released when the jaws 4a, 4b are closed and the electrode members 3a, 3b pass through the tissue and into the ampulla 5 thus releasing the fluid. Simultaneously, the electrode members 3a, 3b are activated and tissue may be coagulated to induce hemostasis. Sensors may be configured and arranged to monitor the amount of heat provided and duration of application. In another example embodiment, while the current is passing between the electrode members 3a, 3b, a driver may advance to form two single rows of staples 2a, 2b on either side of the cutting blade 12. In each of these example embodiments, the stapling mechanism includes a replaceable tray of open staples set within the lower jaw 4b and a set of corresponding staple guides within the upper jaw 4a, such that when the linear clamping mechanism is in a closed position, the open staples immediately oppose the corresponding staple guides. The stapling mechanism further includes a wedge pushing system whereby once the linear clamping mechanism is in a closed position, a wedge riding in a channel below the tray of open staples is pushed through the channel. As the wedge moves through the channel, a sloping surface of the wedge pushes the open staples against the corresponding staple guides, thereby closing the staples. After the staples have been closed, the wedge is pulled back through the channel. The second drive extension pushes or pulls the wedge through the channel, depending on the turning direction of the corresponding motor in the electro-mechanical driver, by engaging a threaded horizontal shaft upon which the wedge, having a matching inner thread, rides.

If the configuration illustrated in FIG. 6 is provided on the inner surfaces of both jaws 4a, 4b, the polarities of electrode members may be the same for both jaws 4a, 4b which may allow current to flow parallel to the respective columns of electrodes. Alternatively, the polarities of the electrode members may be switch between the jaws 4a, 4b, where opposite polarities would exist for the respective corresponding electrode columns between the jaws 4a, 4b which would allow current to flow between jaws 4a, 4b once they are in a closed position.

Figure 7:
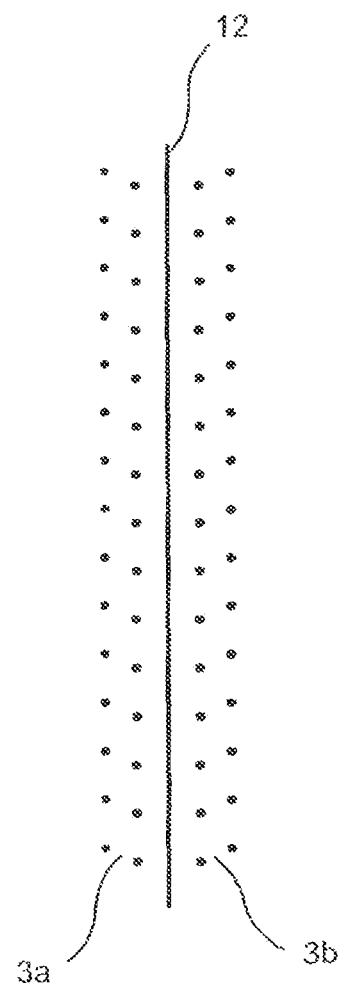
FIG. 7 illustrates another example embodiment of an electrode arrangement according to the present invention.

In another example embodiment of the present invention, staple lines may be removed from the electrode configuration as illustrated in FIG. 7. FIG. 7 illustrated four rows of electrode members 3a, 3b, including two columns are placed on each side of the cutting blade 12. The electrode members may have alternating polarities of RF energy applied in order to produce a current flow. Polarities may alternate vertically or an entire column of electrodes may be positively charged and the respective adjacent column may be negatively charged in order to induce current flow between the two columns on each respective side of cutting blade 12. As described with reference to the electrode configuration illustrated in FIG. 6, the electrode configuration illustrated in FIG. 7 may be placed on both inner surfaces of jaws 4a, 4b. Also, the upper jaw 4a may incorporate pierceable ampulla and function, as described above, with electrode members 3a, 3b as illustrated in FIG. 7.

Figure 8:
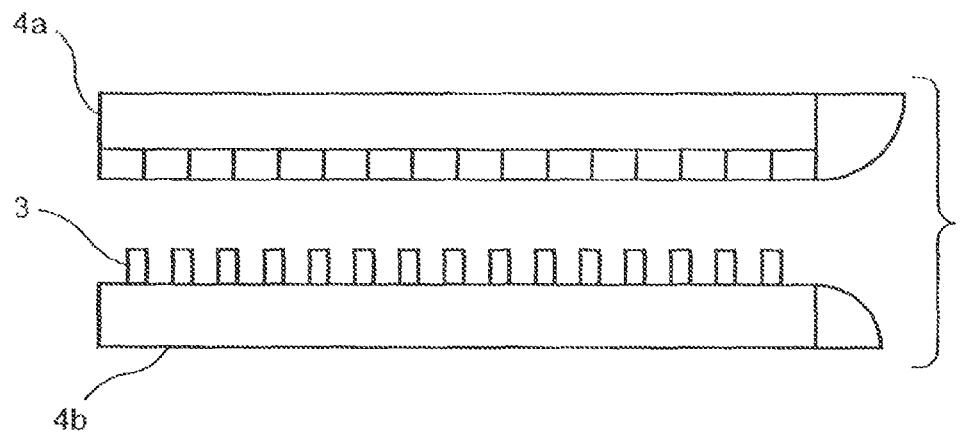
FIG. 8 is a side view of an example electrode configuration according to the present invention.

FIG. 8 is a side view of the jaws 4a, 4b. The electrode members 3 protrude from the lower jaw 4b and are applied to tissue placed between the jaws in order to perform anastomosing, sealing and/or stapling. Accordingly, the electrodes may be rigid, flexible, elastic, inelastic, planar, non-planar, etc., with regard to the material used for their construction. The electrode members 3 may also have features that may enhance tissue penetrating attributes and electrical contact between any opposing electrodes. Various configurations may be employed to enhance contact with tissue where electrode height, width and density of spacing are adjusted in order to accommodate various tissue thickness and texture.

Figure 9:
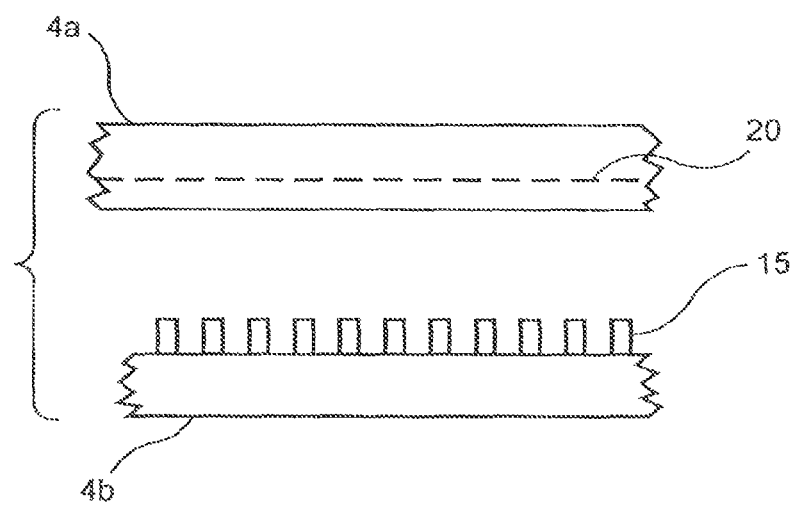
FIG. 9 illustrates an example embodiment of an electrode configuration according to the present invention.

FIG. 9 illustrates an electrode configuration of another example embodiment of the present invention. As illustrated electrode members 15 are disposed over the inner face of the lower jaw 4b. The electrodes 15 are charged positively and receptacles 20 are negatively charged (ground) and configured to align with electrodes 15. This configuration induces current to flow from lower jaw 4b to the upper jaw 4a when the jaws 4a, 4b are closed. The amount of RF energy transferred between jaws 4a, 4b may be varied depending upon whether staples are used in conjunction with the electrodes or if the anastomose is performed solely through the use of the electrode configuration.

Figure 10:
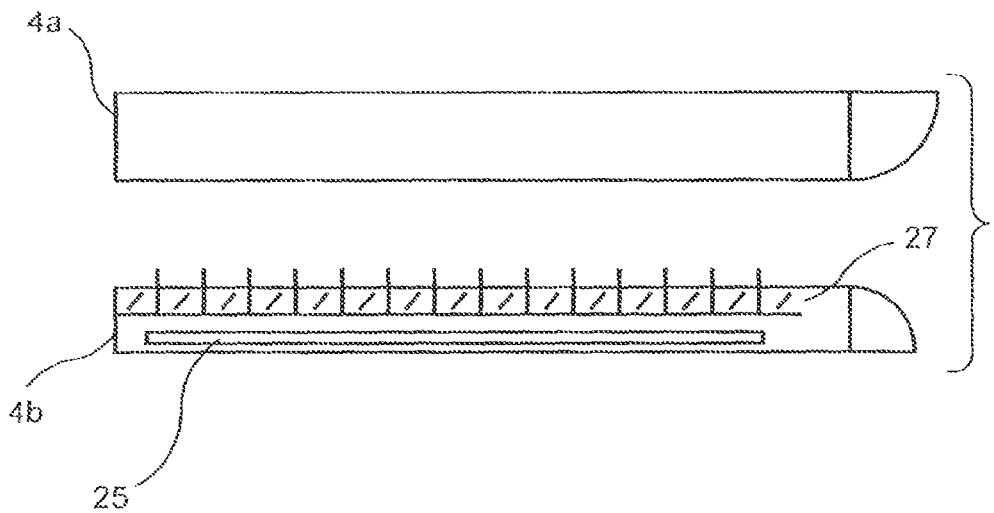
FIG. 10 illustrates an example embodiment of the present invention which includes the use of ultrasonic technology.

FIG. 10 illustrates another example embodiment of the present invention. The electrode configuration illustrated in FIG. 10 provides ultrasonic levels of energy which are transmitted through ultrasonic resonator pins 27 which are configured on the inner surface of the lower jaw 4b. Similar to the electrodes described above, the ultrasonic pins 27 may be configured in various formations conducive to the type and form of the tissue which is placed between the jaws for coagulation, anastomosing and/or cutting. In addition to the ultrasonic resonator pins 27, the lower jaw 4b also includes an ultrasonic transducer 25. The ultrasonic transducer 25 is configured to generate the ultrasonic energy that resonates through the pins 27. The ultrasonic resonator pins 27 may be used with or without staples and as described above with reference to the electrode configurations, enable the reduction of the number of staples used and lessen the mechanical force necessary in order to complete coagulation and cutting.

Figure 11:
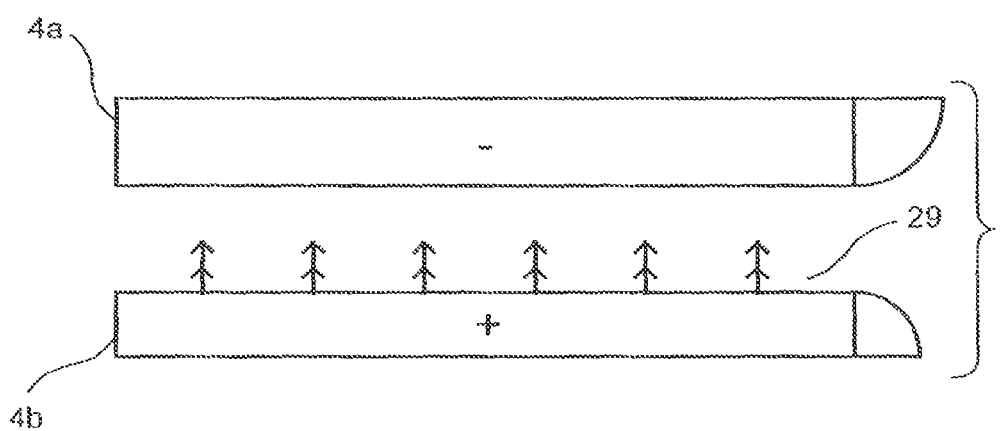
FIG. 11 illustrates an example embodiment where surgical barbs are used as electrodes.

FIG. 11 illustrates another example embodiment of the present invention. The electrodes 29 are configured as surgical barbs. The configuration of electrodes 29 provide for an improved configuration for penetrating tissue. The electrodes 29 may follow the polarity schemes described above in order to apply RF energy to the tissue. The electrodes 29 may be used as illustrated with electrodes arranged on the lower jaw 4b only, however this surgical barb type electrode may be arranged on the inner surface of the upper jaw 4a in order to provide even more effective penetrating results. Furthermore, as described above, pierceable ampulla 5 may be provided in the upper jaw 4a and used to induce hemostasis.

Those skilled in the art will appreciate that numerous modifications of the example embodiment described hereinabove may be made without departing from the spirit and scope of the invention. Although example embodiments and/or example methods of the present invention have been described and disclosed in detail herein, it should be understood that this invention is in no sense limited thereby and that its scope is to be determined by that of the appended claims.

What is claimed is:
1. An electro-mechanical surgical system, comprising:
 a surgical instrument including:
  a first jaw;
  a second jaw opposing the first jaw, the first and second jaws configured to clamp tissue therebetween;
  a plurality of ultrasonic resonator pins arranged on at least one jaw of the first jaw or the second jaw;

a stapling device configured to staple tissue clamped between the first jaw and the second jaw; and an ultrasonic transducer configured to supply ultrasonic energy to the plurality of ultrasonic resonator pins; and an elongated shaft extending from the surgical instrument and having a distal end configured to detachably couple with the surgical instrument.

2. The electro-mechanical surgical system according to claim 1, further comprising a cutting device configured to cut tissue clamped between the first jaw and the second jaw.

3. The electro-mechanical surgical system according to claim 1, wherein the surgical instrument includes at least one sensor configured to sense temperature of tissue.

4. The electro-mechanical surgical system according to claim 3, wherein the at least one sensor is configured to transmit a signal to indicate the temperature of tissue.

5. The electro-mechanical surgical system according to claim 1, wherein at least one jaw of the first jaw or the second jaw includes:

at least one pierceable ampulla containing matter, the at least one pierceable ampulla configured to release the matter when the first jaw and the second jaw are in a closed position; and at least one piercing member, the at least one piercing member configured to pass through the tissue clamped between the first jaw and the second jaw and into the at least one pierceable ampulla.

6. The electro-mechanical surgical system according to claim 5, wherein the matter includes at least one of collagen, fibrin, dye, matter configured to effect anastomosis, matter configured to seal tissue or matter configured to effect hemostasis.

7. The electro-mechanical surgical system according to claim 1, wherein at least one of height, width or density of spacing of the plurality of ultrasonic resonator pins is adjustable.

8. An electro-mechanical surgical device, comprising:

a first jaw;

a second jaw opposing the first jaw, the first and second jaws configured to clamp tissue therebetween;

a plurality of ultrasonic resonator pins, at least one ultrasonic resonator pin of the plurality of ultrasonic resonator pins arranged on at least one jaw of the first jaw or the second jaw;

a plurality of electrodes arranged on at least one of the first jaw or the second jaw, the plurality of electrodes including at least one first electrode and at least one second electrode adjacent to the at least one first electrode, wherein the plurality of resonator pins projects from a tissue contacting surface of the first jaw or the second jaw; and an ultrasonic transducer configured to supply ultrasonic energy to the plurality of ultrasonic resonator pins and to supply electrical energy to the at least one first electrode and the at least one second electrode so that the at least one first electrode has a polarity opposite a polarity of the at least one second electrode.

9. The electro-mechanical surgical device according to claim 8, further comprising a stapling device configured to staple tissue clamped between the first jaw and the second jaw.

10. The electro-mechanical surgical device according to claim 8, further comprising an elongated shaft having a distal end configured to detachably couple with the first jaw and the second jaw.

11. The electro-mechanical surgical device according to claim 8, wherein at least one of height, width or density of spacing of the plurality of ultrasonic resonator pins is adjustable.

12. The electro-mechanical surgical device according to claim 8, further comprising a cutting device configured to cut tissue clamped between the first jaw and the second jaw.

* * * * *